US009650434B2

(12) United States Patent
Chen et al.

(10) Patent No.: US 9,650,434 B2
(45) Date of Patent: May 16, 2017

(54) BROAD-SPECTRUM MONOCLONAL ANTIBODY RECOGNIZING HA1 DOMAIN OF HEMAGGLUTININ OF INFLUENZA VIRUS

(71) Applicant: Xiamen University, Xiamen, Fujian (CN)

(72) Inventors: Yixin Chen, Fujian (CN); Qingbing Zheng, Fujian (CN); Rui Li, Fujian (CN); Chenguang Shen, Fujian (CN); Shaojun Ke, Fujian (CN); Wenxin Luo, Fujian (CN); Honglin Chen, Fujian (CN); Ningshao Xia, Fujian (CN)

(73) Assignee: Xiamen University, Fujian (CN)

( * ) Notice: Subject to any disclaimer, the term of this patent is extended or adjusted under 35 U.S.C. 154(b) by 0 days.

(21) Appl. No.: 14/781,391

(22) PCT Filed: Apr. 2, 2014

(86) PCT No.: PCT/CN2014/074612
§ 371 (c)(1),
(2) Date: Sep. 30, 2015

(87) PCT Pub. No.: WO2014/161483
PCT Pub. Date: Oct. 9, 2014

(65) Prior Publication Data

US 2016/0145320 A1 May 26, 2016

(30) Foreign Application Priority Data

Apr. 2, 2013 (CN) .......................... 2013 1 0113101

(51) Int. Cl.

| | |
|---|---|
| ***C07K 16/10*** | (2006.01) |
| ***G01N 33/569*** | (2006.01) |
| *A61K 39/00* | (2006.01) |

(52) U.S. Cl.
CPC ... *C07K 16/1018* (2013.01); *G01N 33/56983* (2013.01); *A61K 2039/505* (2013.01); *C07K 2317/33* (2013.01); *C07K 2317/34* (2013.01); *C07K 2317/565* (2013.01); *C07K 2317/76* (2013.01); *G01N 2333/11* (2013.01); *G01N 2469/10* (2013.01)

(58) Field of Classification Search
None
See application file for complete search history.

(56) References Cited

U.S. PATENT DOCUMENTS

2012/0058124 A1 3/2012 Kurosawa et al.

FOREIGN PATENT DOCUMENTS

| | | |
|---|---|---|
| CN | 102482345 | 5/2012 |
| WO | 2008028946 | 3/2008 |
| WO | 2010/010467 | 1/2010 |
| WO | 2010132604 | 11/2010 |
| WO | 2012/045001 | 4/2012 |
| WO | 2013/030604 | 3/2013 |

OTHER PUBLICATIONS

PCT/CN2014/074612 International Search Report dated Jun. 25, 2014.

*Primary Examiner* — Shanon A Foley
*Assistant Examiner* — Myron Hill
(74) *Attorney, Agent, or Firm* — Honigman Miller Schwartz and Cohn LLP; Thomas A. Wootton; Jonathan P. O'Brien

(57) ABSTRACT

The invention relates to antibodies recognizing epitopes on HA1 domain of hemagglutinin (HA) protein of influenza virus, cell lines for producing the antibodies, and uses thereof. The antibodies according to the invention can specifically bind to HA1 domain of different HA subtypes and specifically bind to HA1 domain of hemagglutinin (HA) protein of H1 subtype (including seasonal H1N1 and 2009 pandemic H1N1) and H5 subtype of influenza viruses. Therefore, the invention also relates to vaccines or pharmaceutical compositions for preventing and/or treating infection of H1 subtype and H5 subtype influenza virus and/or a disease caused by the infection (e.g. influenza), comprising the antibodies according to the invention.

19 Claims, 5 Drawing Sheets

BROAD-SPECTRUM MONOCLONAL ANTIBODY RECOGNIZING HA1 DOMAIN OF HEMAGGLUTININ OF INFLUENZA VIRUS

CROSS-REFERENCE TO RELATED APPLICATIONS

This application claims priority under 35 U.S.C. §371 to Patent Cooperation Treaty application PCT/CN2014/074612, filed Apr. 2, 2014 which claims the benefit of Chinese patent application no. 201310113101.5, filed Apr. 2, 2013, the entire contents of which are incorporated herein by reference.

SEQUENCE LISTING

This application incorporates by reference in its entirety the Sequence Listing entitled "IEC140009PCTUS_ST25.txt", which is 5.39 kilobytes in size, created on Sep. 29, 2015, and filed electronically herewith.

TECHNICAL FIELD

The invention relates to the field of molecular virology, particularly the field concerning vaccines for the prevention of influenza virus. In particular, the invention relates to antibodies recognizing epitopes on HA1 domain of hemagglutinin of influenza virus, cell lines for producing the antibodies, and uses thereof. The antibodies according to the invention can specifically bind to HA1 domain of different HA subtypes of Influenza virus and specifically bind to HA1 domain of hemagglutinin (HA) protein of H1 subtype (including seasonal H1N1 and 2009 pandemic H1N1) and H5 subtype of influenza viruses. Therefore, the invention also relates to vaccines or pharmaceutical compositions for preventing and/or treating infection of H1 subtype and H5 subtype influenza virus and/or diseases caused by the infection (e.g. influenza), comprising the antibodies according to the invention.

BACKGROUND ART

Influenza, commonly known as "the flu", is a respiratory infectious disease caused by the influenza virus, and has the symptoms of high fever, feeling tired, and muscle pains, accompanied by some respiratory symptoms. Influenza virus is a threat to human health, the sustained and rapid antigenic drift cause wide spread of seasonal influenza. According to statistics of WHO, seasonal influenza is responsible for the death of at least 250,000-500,000 persons per year (Peter D. C. et al., J Clin Invest. 2008, 118:3273-3275). In addition, flu outbreak is still an important threat to human beings. Since influenza virus was discovered, flu outbreak occurred five times around world in human history, resulting in tens of millions of deaths; among them, Spanish influenza (H1N1) in 1918 resulted in about 20-50 millions of deaths in the world. The influenza pandemics occurred in the 20th century also include Asian influenza (H2N2) in 1957 and Hong Kong Influenza (H3N2) in 1968, both of which caused serious public health threat and human social panic (Xu R. et al., Science. 2010, 328: 357-360). In the 21st century, influenza outbreaks still do not stop; influenza A (2009 pandemic H1N1) outbreak occurred in Mexico in 2009 and quickly spreaded around the world, which sounded the alarm to human society once again; according to WHO statistics, up to Aug. 6, 2010, a total of 18,449 cases of confirmed deaths were reported in more than 200 countries and regions globally (WHO Pandemic (H1N1) 2009—update 112. 6 Aug., 2010). In addition, human beings also face the threat of highly pathogenic avian influenza, and highly pathogenic H5N1 avian influenza virus has become one of the greatest infectious diseases that threats human beings, after "SARS" in 2003. Since 2003, 600 cases of human infected by avian influenza virus H5N1 are reported globally, among which 353 cases died, with a mortality rate close to 60% (WHO: http://www.who.int/influenza/human_animal_interface/H5N1_cumulative_table_archives/en/index.html). Due to such a high mortality rate, people can not help but worry that once the virus spreads in human, it will bring a fatal blow to human society.

Influenza virus is an enveloped, single stranded, negative-sense RNA virus that belongs to the genus influenza virus of the family Orthomyxoviridae. Its genome contains eight segments of RNA, and encode for more than 10 viral proteins. According to the difference in antigenicity and genetic characteristics of nucleoprotein (NP) and matrix protein (M), influenza virus can be classified into Influenza virus A, Influenza virus B, and Influenza virus C (Horimoto T. et al., Nat Rev Microbiol, 2005, 3(8): 591-600). Influenza A Virus (called Flu A for short) mutates fast, has a strong pathogenicity, and can cause worldwide pandemics. Influenza B Virus (called Flu B for short) mutates slow and can only cause small pandemics in local areas. Influenza C Virus (called Flu C for short) mutates slowest, has a weak pathogenicity, and can only infect pregnant women and children with a low resistance generally. In nature, there are a broad range of hosts for Flu A. Flu A can cause infection in animals such as human, horses and pigs, in addition to its natural host aquatic birds. Flu A has multiple subtypes which are different from each other greatly, and has become a research focus for influenza control and vaccine.

Flu A viruses are categorized into subtypes based on the antigenicity and genetic characteristics of the two surface antigens, i.e. hemagglutinin (HA) and neuraminidase (NA). There are 17 known HA subtypes (H1 to H17) and 10 known NA subtypes (N1 to N10) (Tong S. X. et al., PNAS. 2012, 109(11):4269-74). The Flu A subtypes epidemic in human beings include two HA subtypes (H1, H3) and two NA subtypes (N1, N2). Although highly pathogenic avian influenza virus H5N1 only infects human beings occasionally, it draws attention due to the high mortality rate.

The first line of defense to prevent influenza is neutralizing antibodies. The vaccine-induced neutralizing antibodies mainly target the membrane protein hemagglutinin (HA) on the surface of virus. HA protein on the surface of virus has a trimeric structure, and each HA monomer consists of HA1 domain and HA2 domain. HA1 forms a globule at the top of the trimer, contains receptor binding sites, and is a region essential for the virus to infect a host cell; HA1 also contains important antigenic sites, can induce generation of protective neutralizing antibodies in organisms, and thus is a key target for vaccine design (Wang T. T. et al., Nat Struct Mol Biol. 2009, 16: 233-234). HA2 is located at the base of the trimer, has a shape of stem, contains fusion peptide, and can mediate the fusion of viral envelope to host cell membrane; and some monoclonal antibodies against HA2 can inhibit the membrane fusion of influenza virus so as to achieve the effect of neutralizing virus (Wang T. T. et al., Nat Struct Mol Biol. 2009, 16: 233-234).

Influenza viruses have a high variability, particularly, HA mutates fastest. In current, traditional influenza vaccines are mainly directed to HA protein, and the influenza vaccines become ineffective easily because of virus antigenic drift caused by HA gene mutation. In order to keep influenza vaccines effective, WHO annually needs to monitor the mutation of the influenza virus strains epidemic last year, and select old influenza virus vaccines or establish new influenza virus vaccines as candidate influenza vaccines next year so as to retain the effective protection from epidemic influenza virus strains by inoculation of new vaccines every year. Therefore, development of "universal influenza vaccines" that are not affected by virus mutation becomes a research focus for development of new vaccines. The glycoprotein on the surface of influenza virus, i.e. "hemagglutinin (HA)", is a main target for the development of universal influenza vaccines and immunotherapeutic medicines against influenza virus. The so-called "universal influenza vaccines" should comprise "highly conserved neutralizing epitopes" shared by different viral mutants, and can directly induce the generalization of "broad-spectrum neutralizing antibodies" to combat the infection by different virus mutants. Therefore, an important route for studying universal influenza vaccines and immunotherapeutic medicines against influenza is to look for highly conserved neutralizing epitopes on HA.

In addition, in a mouse animal model, a humanized HA monoclonal antibody specific to H1N1 and H5N1 has been demonstrated to be able to effectively treat experimental mice infected by influenza virus (Corti D. et al., J Clin Invest. 2010, 120:1663-1673). In clinic, polyclonal antibodies and monoclonal antibodies can be effectively applied to the prevention of infections by viruses such as Hepatitis A Virus, Hepatitis B Virus, rabies virus and respiratory syncytial virus (Sawyer L. A. et al., Antiviral Res. 2000, 47: 57-77). During Spanish influenza in 1918, it was reported that serum from human in convalescent stage was used for the treatment (Luke T. C. et al., Ann Intern Med. 2006, 145:599-609). The information suggests that antibodies can be used as alternative methods and tools for anti-viral therapy.

HA broad-spectrum monoclonal antibodies and highly conserved epitopes have been reported in many papers. Studies on broad-spectrum monoclonal antibodies and highly conserved epitopes against HA2 which is more conservative have become a major research focus (Throsby M. et al., PLoS One. 2009, 3: e3942; Sui J. et al., Nat Struct Mol Biol. 2009, 16: 265-273; Corti D. et al., J Clin Invest. 2010, 120: 1663-1673; Corti D. et al., Science. 2011, 333: 850-856). As early as 2009, Throsby et al. reported for the first time that a broad-spectrum neutralizing humanized monoclonal antibody CR6261 recognizing HA2 could neutralize all the influenza viruses belonging to Group 1 (including H1, H2, H5, H6, H8 and H9 subtypes) (Throsby M. et al., PLoS One. 2009, 3: e3942). In 2011, *Corti* D. et al. also obtained a humanized broad-spectrum neutralizing monoclonal antibody against HA2 by similar technology, which could neutralize 16 types of H subtype influenza viruses (Corti D. et al., Science. 2011, 333: 850-856), and became one of the most broad-spectrum neutralizing monoclonal antibodies against influenza reported recently. The discovery of these broad-spectrum monoclonal antibodies provides new hope for the development of broad-spectrum therapeutic monoclonal antibodies and universal influenza vaccines against influenza virus. The epitopes recognized by the monoclonal antibodies obtained in said studies are all located in a conservative region surrounding the fusion peptide on HA2, the main function of which is to mediate the membrane fusion of influenza virus, and the monoclonal antibodies do not recognize HA1 domain that have immune predominance. Therefore, it increases the uncertainty in the prospect of applying these antibodies and the recognized conservative epitopes to the treatment and prevention. Some studies show that the neutralizing monoclonal antibodies recognizing HA2 have a neutralizing activity reduced by 100-1000 folds for natural virus, as compared to pseudovirus, which may be due to the fact that the HA2 epitope of natural virus is not easily exposed and is difficult to be approached (Sui J. et al., Nat Struct Mol Biol. 2009, 16: 265-273; Corti D. et al., J Clin Invest. 2010, 120: 1663-1673).

As compared to HA2, HA1 of influenza virus forms a globule at the top of the trimer, contains a lot of neutralizing epitopes, and is easily accessible. Therefore, it is more possible to develop effective universal influenza vaccines and therapeutic antibodies by looking for highly conserved neutralizing epitopes on HA1. Since the subtypes of influenza virus are divided initially based on stereotyping of polyclonal antibodies and the pAb serum against one subtype has little cross-reactivity with virus of another subtype, it is generally believed that the neutralizing monoclonal antibodies specific to HA (particularly HA1) are serotype-specific and has no cross-reactivity with HA of another subtype. However, it is also found in some researches recently that the highly conserved neutralizing epitopes on HA1 can induce the generation of broad-spectrum monoclonal antibodies having cross-subtypes reactivity (Yoshida R. et al., PLoS Pathog. 2009, 5: e1000350; Krause J. C. et al., J Virol. 2011, 85: 10905-10908; Wrammert J. et al., J Exp Med. 2011, 208: 181-193). Since HA1 has a high variability, the reactive spectrum of the current HA1 monoclonal antibodies is narrow, as compared to that of HA2 monoclonal antibodies, and the HA1 monoclonal antibodies generally have a cross-neutralizing activity for 2-3 subtypes of influenza viruses. Yoshida et al. reported in 2008 that a HA1 broad-spectrum neutralizing monoclonal antibody, S139/1, could neutralize H1, H2, H3 and H13 subtypes of influenza viruses, but the neutralizing activity of the monoclonal antibody was only limited to a few virus strains for each of said subtypes (Yoshida R. et al., PLoS Pathog. 2009, 5: e1000350). After the 2009 pandemic H1N1 outbreak in 2009, many papers reported cross-neutralizing monoclonal antibodies against 2009 pandemic H1N1 and seasonal H1N1 influenza viruses, including the cross-neutralizing monoclonal antibody against 2009 pandemic H1N1 and H1N1 of 1918 (Krause J. C. et al., J Virol. 2010, 84: 3127-3130; Xu K. et al., Viral Immunol. 2011, 24: 45-56), and the cross-neutralizing monoclonal antibody against 2009 pandemic H1N1 and seasonal H1N1 epidemic recently (Krause J. C. et al., J Virol. 2011, 85: 10905-10908; Wrammert J. et al., J Exp Med. 2011, 208: 181-193). In addition, when screening a broad-spectrum neutralizing monoclonal antibody against HA2, Corti et al. also obtained a cross-neutralizing monoclonal antibody FE17 against HA1, which could cross-neutralize seasonal H1 and H5 subtypes of influenza viruses, and the epitope of which was located close to Ca2 antigenic region. These studies show that HA1 may contain conservative neutralizing epitopes, which are important for the research on universal influenza vaccines and immunotherapeutic medicines. Therefore, it is of importance and instructiveness for the development of broad-spectrum therapeutic antibodies and universal influenza vaccines against influenza, to look for broad-spectrum neutralizing monoclonal antibodies that recognize more highly conserved neutralizing epitopes on HA1 and to accurately localize the epitopes.

CONTENTS OF INVENTION

In the invention, unless otherwise specified, the scientific and technical terms used herein have the meanings as generally understood by a person skilled in the art. Moreover, the laboratory operations of cell culture, molecular genetics, nucleic acid chemistry and immunology used herein are the routine operations widely used in the corresponding fields. Meanwhile, in order to better understand the invention, the definitions and explanations of the relevant terms are provided as follows.

As used herein, the term "H3 numbering" refers to the numbering based on the amino acid sequence of the HA obtained by aligning the HA amino acid sequence of H1N1 virus with the amino acid sequence of HA (with the signal peptide removed) of H3N2 virus strain A/Hong Kong/1/1968 (H3N2) (Genbank: AAK51718.1). Therefore, as used herein, the amino acid residue at position N (such as position 142) of HA refers to the amino acid residue corresponding to the one at position N (such as position 142) of the amino acid sequence of the aligned HA.

As used herein, the term "antibody" generally refers to an immunoglobulin molecule consisting of two pairs of polypeptide chains (each has a light (L) chain and a heavy (H) chain). Light chains of an antibody may be classified into K and A light chain. Heavy chains may be classified into $\mu$, $\delta$, $\gamma$, $\alpha$ and $\epsilon$, which define isotypes of an antibody as IgM, IgD, IgG, IgA and IgE, respectively. In a light chain and a heavy chain, a variable region is linked to a constant region via a "J" region of about 12 or more amino acids, and a heavy chain further comprises a "D" region of about 3 or more amino acids. Each heavy chain consists of a heavy chain variable region (VH) and a heavy chain constant region (CH). A heavy chain constant region consists of 3 domains (CH1, CH2 and CH3). Each light chain consists of a light chain variable region (VL) and a light chain constant region (CL). A light chain constant region consists of a domain CL. The constant region of an antibody can mediate the binding of an immunoglobulin to a host tissue or factor, including various cells (e.g., effector cells) of an immune system and the first component (C1q) of classical complement system. VH and VL region can also be divided into hypervariable regions (called complementary determining regions (CDR)), which are interspaced by relatively conservative regions (called framework region (FR)). Each VH and VL consists of 3 CDRs and 4 FRs in the following order: FR1, CDR1, FR2, CDR2, FR3, CDR3, FR4 from N-terminal to C-terminal. The variable region (VH and VL) of each heavy/light chain pair forms an antigen binding site, respectively. Distribution of amino acids in various regions or domains follows the definition in Kabat Sequences of Proteins of Immunological Interest (National Institutes of Health, Bethesda, Md. (1987 and 1991)), or Chothia & Lesk (1987) J. Mol. Biol. 196:901-917; Chothia et al., (1989) Nature 342:878-883. The term "antibody" is not restricted by any specific method for producing antibodies. For example, antibodies include particularly, recombinant antibodies, monoclonal antibodies and polyclonal antibodies. Antibodies may be of different antibody isotypes, for example, IgG (e.g., IgG1, IgG2, IgG3 or IgG4 subtype), IgA1, IgA2, IgD, IgE or IgM antibody.

As used herein, the term "antigen binding fragment" of an antibody refers to polypeptides comprising fragments of a full-length antibody, which retain the ability of specifically binding to an antigen that the full-length antibody specifically binds to, and/or compete with the full-length antibody for binding to the same antigen, also known as "antigen binding portion". Generally, see Fundamental Immunology, Ch. 7 (Paul, W., ed., the second edition, Raven Press, N.Y. (1989), which is incorporated herein by reference for all purposes. Antigen binding fragments of an antibody may be produced by recombinant DNA techniques or by enzymatic or chemical cleavage of an intact antibody. Under some conditions, antigen binding fragments include Fab, Fab', F(ab')2, Fd, Fv, dAb and complementary determining region (CDR) fragments, single chain antibody (e.g. scFv), chimeric antibody, diabody and such polypeptides that comprise at least a part of an antibody sufficient to confer the ability of specific binding with the antigen to the polypeptides.

As used herein, the term "Fd fragment" refers to an antibody fragment consisting of VH and CH1 domain; the term "Fv fragment" refers to an antibody fragment consisting of VL and VH domain of a single arm; the term "dAb fragment" refers to an antibody fragment consisting of VH domain (Ward et al., Nature 341:544-546 (1989)); the term "Fab fragment" refers to an antibody fragment consisting of VL, VH, CL and CH1 domain; the term "F(ab')2 fragment" refers to an antibody fragment comprising two Fab fragments linked to each other via disulphide bridge(s) on hinge region.

Under some conditions, antigen binding fragments of an antibody are single chain antibodies (e.g. scFv), wherein VL and VH domain are paired to form a monovalent molecule via a linker that enables them to produce a single polypeptide chain (see, for example, Bird et al., Science 242:423-426 (1988) and Huston et al., Proc. Natl. Acad. Sci. USA 85:5879-5883 (1988)). Such scFv molecules generally have a common structure: NH2-VL-linker-VH-COOH or NH2-VH-linker-VL-COOH. Suitable linkers in the prior art consist of repeated GGGGS amino acid sequence or variants thereof. For example, a linker having an amino acid sequence (GGGGS)4 may be used, and its variants may also be used (Holliger et al., (1993), Proc. Natl. Acad. Sci. USA 90: 6444-6448). Other linkers that may be used in the invention are described by Alfthan et al., (1995), Protein Eng. 8:725-731, Choi et al., (2001), Eur. J. Immunol. 31: 94-106, Hu et al., (1996), Cancer Res. 56:3055-3061, Kipriyanov et al., (1999), J. Mol. Biol. 293:41-56 and Roovers et al., (2001), Cancer Immunol.

Under some conditions, antigen binding fragments of an antibody may be diabodies, i.e. divalent antibodies, wherein VH and VL domain are expressed on a single polypeptide chain, however, the linker used is too short to allow the pairing of the two domains on the same chain, the domains have to be paired with the complementary domains on another chain to produce two antigen binding sites (see, for example, Holliger P. et al., Proc. Natl. Acad. Sci. USA 90:6444-6448 (1993), and Poljak R. J. et al., Structure 2:1121-1123 (1994)).

Antigen binding fragments (e.g. the antibody fragments as described above) of an antibody may be obtained from a given antibody (e.g., the monoclonal antibody provided in the invention) by conventional techniques known by a person skilled in the art (e.g., recombinant DNA technique or enzymatic or chemical cleavage methods), and may be screened for specificity in the same manner by which intact antibodies are screened.

In the invention, unless specified definitely, when the term "antibody" is mentioned, it includes not only intact antibodies, but also antigen binding fragments of the antibodies.

As used herein, the term "mAb" and "monoclonal antibody" refer to an antibody or a fragment of an antibody from a population of highly homologous antibody molecules, i.e. a population of completely identical antibody molecules except for natural mutation that may occur spontaneously. A monoclonal antibody has a high specificity for a single epitope of an antigen. Polyclonal antibody, relative to monoclonal antibody, generally comprises at least two or more different antibodies which generally recognize different epitopes on an antigen. Monoclonal antibodies are generally obtained by hybridoma technique reported by Kohler et al. for the first time (Nature, 256:495, 1975), and can also be obtained by recombinant DNA technique (see, for example, U.S. Pat. No. 4,816,567).

For example, monoclonal antibodies may be prepared as follows. Firstly, mice or other suitable host animals are immunized by injection of immunogen (if necessary, adjuvants are added). The injection means of immunogens or adjuvants generally are subcutaneous multi-point injection or intraperitoneal injection. Pre-conjugation of immunogens to some known proteins (e.g. serum albumin or soybean trypsin inhibitor) may promote immunogenicity of antigens in a host. Adjuvants may be Freund's adjuvant or MPL-TDM, etc. After immunization of animal, lymphocytes secreting antibodies that specifically bind to immunogen are produced in the animal. In addition, lymphocytes may be obtained by means of in vitro immunization. Lymphocytes of interest are collected and are fused to myeloma cells using a suitable fusion agent (such as PEG), thereby getting hybridoma cells (Goding, Monoclonal Antibodies: Principles and Practice, pp. 59-103, Academic Press, 1996). The hybridoma cells prepared above are seeded to a suitable culture medium and grow in the medium, and the culture medium comprises one or more substances capable of inhibiting growth of unfused, parent myeloma cells. For example, in the case of parent myeloma cells deficient in hypoxanthine guanine phosphoribosyl transferase (HGPRT or HPRT), growth of HGPRT-deficient cells is inhibited by the addition of substances such as hypoxanthine, aminopterin and thymine (HAT culture medium) to the culture medium. Preferred myeloma cells should have a high fusion rate, stable ability of secreting antibodies, be sensitive to HAT culture medium, and the like. The first choice of myeloma cells is murine myeloma, such as MOP-21 and MC-11 mouse tumor derived cell line (THE Salk Institute Cell Distribution Center, San Diego, Calif. USA), and SP-2/0 or X63-Ag8-653 cell line (American Type Culture Collection, Rockville, Md. USA). In addition, human myeloma and human-mouse heterogenous myeloma cell lines may be used to prepare human monoclonal antibodies (Kozbor, J. Immunol., 133: 3001 (1984); Brodeur et al., Monoclonal Antibody Production Techniques and Applications, pp. 51-63, Marcel Dekker, Inc., New York, 1987). Culture media for growing hybridoma cells are used to detect the generation of monoclonal antibodies against specific antigens. The following methods may be used to determine the binding specificity of monoclonal antibodies produced in hybridoma cells, immunoprecipitation or in vitro binding assays, such as Radioimmunoassay (RIA) and enzyme linked immunosorbent assay (ELISA). For example, Scatchard assay described in Munson et al., Anal. Biochem. 107: 220 (1980) may be used to determine the affinity of monoclonal antibodies. After determining the specificity, affinity and reactivity of antibodies produced in hybridomas, cell lines of interest may be subcloned by limiting dilution method described in Goding, Monoclonal Antibodies: Principles and Practice, pp. 59-103, Academic Press, 1996. A suitable culture medium may be DMEM or RPMI-1640, etc. In addition, hybridoma cells may grow in a form of ascites tumor in animal bodies. By using traditional methods for purifying immunoglobulins, such as Protein A agarose gel, hydroxyapatite chromatography, gel electrophoresis, dialysis and affinity chromatography, monoclonal antibodies secreted by subclone cells may be isolated from cell culture, ascites or serum.

Monoclonal antibodies may be obtained by genetic engineering recombinant techniques. The nucleic acid primers that specifically bind to MAb heavy chain and light chain gene are subjected to PCR amplification, thereby isolating the DNA molecules encoding MAb heavy chain and light chain from hybridoma cells. The DNA molecules obtained are inserted into an expression vector, host cells (e.g. *E. coli* cells, COS cells, CHO cells, or other myeloma cells that do not produce immunoglobulin) are transfected with them and are cultured under suitable conditions to obtain antibodies of interest by recombinant expression.

As used herein, the term "chimeric antibody" refers to such an antibody wherein a part of its light chain and/or heavy chain is derived from an antibody (which may be originated from a specific species or belongs to a specific antibody type or subtype), and the other part of its light chain and/or heavy chain is derived from another antibody (which may be originated from an identical or different species or belongs to an identical or different antibody type or subtype), provided that the antibody still retains the activity of binding to the antigen of interest (U.S. Pat. No. 4,816,567 to Cabilly et al.; Morrison et al., Proc. Natl. Acad. Sci. USA, 81: 6851-6855 (1984)).

As used herein, the term "humanized antibody" refers to an antibody or antibody fragment in which all the CDR regions or a part of CDR regions of human immunoglobulin (receptor antibody) are replaced with the CDR regions of a non-human antibody (donor antibody), wherein the donor antibody may be non-human (e.g., mouse, rat or rabbit) antibody having the expected specificity, affinity or reactivity. In addition, some amino acids of framework regions (FRs) of a receptor antibody may also be replaced by the corresponding amino acid residues of a non-human antibody, or amino acid residues of another antibody, so as to further improve or optimize the properties of the antibody. With respect to more detailed contents relating to humanized antibodies, see, for example, Jones et al., Nature, 321:522-525 (1986); Reichmann et al., Nature, 332:323-329 (1988); Presta, Curr. Op. Struct. Biol., 2:593-596 (1992); and Clark, Immunol. Today 21: 397-402 (2000).

As used herein, the term "neutralization antibody" refers to an antibody or antibody fragment that can eliminate or significantly reduce virulence (e.g. ability of infecting cells) of viruses of interest.

As used herein, the term "epitope" refers to a portion on antigen that an immunoglobulin or antibody specifically binds to. "Epitope" is also known as "antigenic determinant". Eptiope or antigenic determinant generally consists of chemically active surface groups of a molecule such as amino acids, carbohydrates or sugar side chains, and generally has a specific three-dimensional structure and a specific charge characteristic. For example, an epitope generally comprises at least 3, 4, 5, 6, 7, 8, 9, 10, 11, 12, 13, 14 or 15 consecutive or non-consecutive amino acids in a unique steric conformation, which may be "linear" or "conformational". See, for example, Epitope Mapping Protocols in Methods in Molecular Biology, Vol. 66, G. E. Morris, Ed. (1996). In a linear epitope, all the interaction sites between a protein and an interaction molecule (e.g., an antibody) are present linearly along the primary amino acid sequence of the protein. In a conformational epitope, the interaction sites span over amino acid residues that are separate from each other in a protein.

As used herein, the term "epitope peptide" refers to peptide fragment on antigen that acts as epitope. Under some conditions, epitope peptide alone can be specifically recognized/bound by an antibody against the epitope. Under some other conditions, epitope peptide has to be fused to a carrier protein to facilitate the epitope to be specifically recognized by an antibody. As used herein, the term "carrier protein" refers to such a protein that may act as a carrier of epitope peptide, i.e. the epitope peptide may be inserted into the protein at a specific position (for example, inner, N-terminal or C-terminal of the protein), so that the epitope peptide can be presented and thus can be recognized by an antibody or immune system. Such carrier proteins are well known by a person skilled in the art, including, for example, HPV L1 protein (into which the epitope peptide may be inserted between amino acids from positions 130 to 131 or amino acids from positions 426 to 427 of the protein, see Slupetzky, K. et al., Chimeric papillomavirus-like particles expressing a foreign epitope on capsid surface loops [J]. J Gen Virol, 2001, 82: 2799-2804; Varsani, A. et al., Chimeric human papillomavirus type 16 (HPV-16) L1 particles presenting the common neutralizing epitope for the L2 minor capsid protein of HPV-6 and HPV-16 [J]. J Virol, 2003, 77: 8386-8393), HBV core antigen (the amino acids from positions 79 to 81 of the protein may be replaced with the epitope peptide, see, Koletzki, D., et al. HBV core particles allow the insertion and surface exposure of the entire potentially protective region of Puumala hantavirus nucleocapsid protein [J]. Biol Chem, 1999, 380: 325-333), woodchuck hepatitis virus core protein (the amino acids from positions 79 to 81 of the protein may be replaced with the epitope peptide, see, Sabine Konig, Gertrud Beterams and Michael Nassal, J. Virol. 1998, 72(6):4997), and CRM197 protein (the epitope peptide may be linked to the N-terminal or C-terminal of the protein or a fragment thereof). Optionally, a linker (e.g., a flexible or rigid linker) may be used between an epitope peptide and a carrier protein to promote their folding, respectively.

Antibodies may be screened depending on competitiveness of binding to the same epitope by conventional techniques known by a person skilled in the art. For example, study on competition or cross-competition may be conducted to obtain antibodies that compete or cross-compete with each other for binding to antigens (e.g. influenza virus HA protein). High-throughput methods for obtaining antibodies binding to the same epitope, which are based on their cross-competition, are described in an international patent application WO 03/48731. Therefore, antibodies and antigen binding fragments (i.e. antigen binding portions) thereof, which compete with monoclonal antibodies according to the invention (e.g. monoclonal antibody 12H5, or G10D10 or 8F11) for binding to the same epitopes on influenza virus HA protein, can be obtained by conventional techniques known by a person skilled in the art.

As used herein, the term "isolated" refers to a state obtained from natural state by artificial means. If a certain "isolated" substance or component is present in nature, it is possible because its natural environment changes, or the substance is isolated from natural environment, or both. For example, a certain unisolated polynucleotide or polypeptide naturally exists in a certain living animal body, and the same polynucleotide or polypeptide with a high purity isolated from such a natural state is called isolated polynucleotide or polypeptide. The term "isolated" excludes neither the mixed artificial or synthesized substance nor other impure substances that do not affect the activity of the isolated substance.

As used herein, the term "*E. coli* expression system" refers to an expression system consisting of *E. coli* (strain) and a vector, wherein the *E. coli* (strain) are derived from the commercially available strains, including, but not limited to: GI698, ER2566, BL21 (DE3), B834 (DE3), and BLR (DE3).

As used herein, the term "vector" refers to a nucleic acid vehicle which can have a polynucleotide inserted therein. When the vector allows for the expression of the protein encoded by the polynucleotide inserted therein, the vector is called an expression vector. The vector can have the carried genetic material elements expressed in a host cell by transformation, transduction, or transfection into the host cell. Vectors are well known by a person skilled in the art, including, but not limited to plasmids, phages, cosmids, artificial chromosome such as yeast artificial chromosome (YAC), bacterial artificial chromosome (BAC) or P1-derived artificial chromosome (PAC); phage such as A phage or M13 phage and animal virus. The animal viruses that can be used as vectors, include, but are not limited to, retrovirus (including lentivirus), adenovirus, adeno-associated virus, herpes virus (such as herpes simplex virus), pox virus, baculovirus, papillomavirus, papova virus (such as SV40). A vector may comprises multiple elements for controlling expression, including, but not limited to, a promoter sequence, a transcription initiation sequence, an enhancer sequence, a selection element and a reporter gene. In addition, a vector may comprise origin of replication.

As used herein, the term "host cell" refers to a cell into which a vector can be introduced, including, but not limited to, prokaryotic cell such as *E. coli* or *Bacillus subtilis*, fungal cell such as yeast cell or *Aspergillus*, insect cell such as S2 *Drosophila* cell or Sf9, and animal cell such as fibroblast, CHO cell, COS cell, NSO cell, HeLa cell, BHK cell, HEK 293 cell or human cell.

As used herein, the term "identity" refers to the match degree between two polypeptides or between two nucleic acids. When two sequences for comparison have the same base or amino acid monomer sub-unit at a certain site (e.g., each of two DNA molecules has an adenine at a certain site, or each of two polypeptides has a lysine at a certain site), the two molecules are identical at the site. The percent identity between two sequences is a function of the number of identical sites shared by the two sequences over the total number of sites for comparison×100. For example, if 6 of 10 sites of two sequences are matched, these two sequences have an identity of 60%. For example, DNA sequences: CTGACT and CAGGTT share an identity of 50% (3 of 6 sites are matched). Generally, the comparison of two sequences is conducted in a manner to produce maximum identity. Such alignment can be conducted by using a computer program such as Align program (DNAstar, Inc.) which is based on the method of Needleman, et al. (J. Mol. Biol. 48:443-453, 1970). The percent identity between two amino acid sequences can be determined using the algorithm of E. Meyers and W. Miller (Comput. Appl. Biosci., 4:11-17 (1988)) which has been incorporated into the ALIGN program (version 2.0), using a PAM120 weight residue table, a gap length penalty of 12 and a gap penalty of 4. In addition, the percentage of identity between two amino acid sequences can be determined by the algorithm of Needleman and Wunsch (J. Mol. Biol. 48:444-453 (1970)) which has been incorporated into the GAP program in the GCG software package (available at http://www.gcg.com), using either a Blossum 62 matrix or a PAM250 matrix, and a gap weight of 16, 14, 12, 10, 8, 6, or 4 and a length weight of 1, 2, 3, 4, 5, or 6.

As used herein, the term "conservative substitution" refers to amino acid substitutions which would not disadvantageously affect or change the essential properties of a protein/polypeptide comprising the amino acid sequence. For example, a conservative substitution may be introduced by standard techniques known in the art such as site-directed mutagenesis and PCR-mediated mutagenesis. Conservative amino acid substitutions include substitutions wherein an amino acid residue is substituted with another amino acid residue having a similar side chain, for example, a residue physically or functionally similar (such as, having similar size, shape, charge, chemical property including the capability of forming covalent bond or hydrogen bond, etc.) to the corresponding amino acid residue. The families of amino acid residues having similar side chains have been defined in the art. These families include amino acids having alkaline side chains (for example, lysine, arginine and histidine), amino acids having acidic side chains (for example, aspartic acid and glutamic acid), amino acids having uncharged polar side chains (for example, glycine, asparagine, glutamine, serine, threonine, tyrosine, cysteine, tryptophan), amino acids having nonpolar side chains (for example, alanine, valine, leucine, isoleucine, proline, phenylalanine, methionine), amino acids having β-branched side chains (such as threonine, valine, isoleucine) and amino acids having aromatic side chains (for example, tyrosine, phenylalanine, tryptophan, histidine). Therefore, a corresponding amino acid residue is preferably substituted with another amino acid residue from the same side-chain family. Methods for identifying amino acid conservative substitutions are well known in the art (see, for example, Brummell et al., Biochem. 32: 1180-1187 (1993); Kobayashi et al., Protein Eng. 12(10): 879-884 (1999); and Burks et al., Proc. Natl. Acad. Sci. USA 94: 412-417 (1997), which are incorporated herein by reference).

As used herein, the term "immunogenicity" refers to ability of stimulating the formation of specific antibodies or sensitized lymphocytes in organisms. It not only refers to the property of an antigen to stimulate a specific immunocyte to activate, proliferate and differentiate so as to finally generate immunologic effector substance such as antibody and sensitized lymphocyte, but also refers to the specific immune response that antibody or sensitized T lymphocyte can be formed in immune system of an organism after stimulating the organism with an antigen. Immunogenicity is the most important property of an antigen. Whether an antigen can successfully induce the generation of an immune response in a host depends on three factors, properties of an antigen, reactivity of a host, and immunization means.

As used herein, the term "specifically bind" refers to the binding of two molecules in a non-random manner, such as the reaction between an antibody and the antigen it directs to. In some embodiments, an antibody that specifically binds to an antigen (or an antibody specific for an antigen) refers to an antibody that binds to the antigen with an affinity (KD) of less than about 10-5 M, e.g. of less than about 10-6 M, 10-7 M, 10-8 M, 10-9 M or 10-10 M or less.

As used herein, the term "KD" refers to a dissociation equilibrium constant of a specific antibody-antigen interaction, which is used to describe the binding affinity of an antibody to an antigen. The smaller the dissociation equilibrium constant is, the more closely the antibody binds to the antigen and the higher the affinity of the antibody to the antigen is. Generally, an antibody (e.g., the monoclonal antibody 12H5, G10D10 or 8F11 according to the invention) binds to an antigen (e.g., influenza virus HA protein) with a KD of less than about 10-5 M, e.g., less than about 10-6 M, 10-7 M, 10-8 M, 10-9 M or 10-10 M or less, determined by, for example, surface plasmon resonance (SPR) in BIACORE device.

As used herein, the term "monoclonal antibody" and the term "MAb" have the same meanings and are used interchangeably; the term "polyclonal antibody" and the term "PAb" have the same meanings and are used interchangeably; the term "polypeptide" and "protein" have the same meanings and are used interchangeably. Moreover, in the invention, amino acids are generally represented by single letter codes or three letter codes. For example, alanine may be represented by A or Ala.

As used herein, the term "hybridoma" and the term "hybridoma cell line" may be used interchangeably. When the term "hybridoma" and the term "hybridoma cell line" are mentioned, they also include subclone and progeny cell of hybridoma. For example, when hybridoma cell line 12H5, G10D10 or 8F11 is mentioned, it also refers to the subclone and progeny cell of hybridoma cell line 12H5, G10D10 or 8F11.

As used herein, the term "a pharmaceutically acceptable carrier and/or excipient" refers to a carrier and/or excipient pharmacologically and/or physiologically compatible with a subject and an active agent, which is well known in the art (see, e.g., Remington's Pharmaceutical Sciences. Edited by Gennaro A R, 19th ed. Pennsylvania: Mack Publishing Company, 1995), and includes, but is not limited to pH adjuster, surfactant, adjuvant and ionic strength enhancer. For example, the pH adjuster includes, but is not limited to, phosphate buffer; the surfactant includes, but is not limited to, cationic, anionic, or non-ionic surfactant, e.g., Tween-80; the ionic strength enhancer includes, but is not limited to, sodium chloride.

As used herein, the term "adjuvant" refers to a non-specific immunopotentiator, which can enhance immune response to an antigen or change the type of immune response in an organism when it is delivered together with the antigen to the organism or is delivered to the organism in advance. There are a variety of adjuvants, including, but not limited to, aluminum adjuvants (for example, aluminum hydroxide), Freund's adjuvants (for example, Freund's complete adjuvant and Freund's incomplete adjuvant), coryne bacterium parvum, lipopolysaccharide, cytokines, and the like. Freund's adjuvant is the most commonly used adjuvant in animal experiments now. Aluminum hydroxide adjuvant is more commonly used in clinical trials.

As used herein, the term "protein vaccine" refers to a polypeptide-based vaccine, optionally comprising an adjuvant. Polypeptides in vaccines may be obtained by genetic engineering techniques or by methods of chemical synthesis. As used herein, the term "nucleic acid vaccine" refers to a DNA or RNA-based vaccine (such as plasmid, e.g., expression plasmid), optionally comprising an adjuvant.

As used herein, the term "an effective amount" refers to an amount that is sufficient to achieve or at least partially achieve the expected effect. For example, an amount effective for preventing a disease (such as influenza virus infection or diseases associated with influenza virus infection) refers to an amount effective for preventing, suppressing, or delaying the occurrence of a disease (such as influenza virus infection or diseases associated with influenza virus infection). An effective amount for treating a disease refers to an amount effective for curing or at least partially blocking a disease and its complication in a patient having the disease. The determination of such an effective amount is within the ability of a person skilled in the art. For example, an amount effective for a therapeutic use depends on severity of a disease to be treated, general state of the immune system in a patient, general conditions of a patient, such as age, weight and gender, administration means of drugs, additional therapies used simultaneously, and the like.

The inventor surprisingly found by conducting a lot of experimental researches that there were highly conserved epitopes in HA1 domain of surface antigen HA protein of influenza virus H1N1, and antibodies recognizing these epitopes could specifically bind to HA1 domain of different HA subtypes of influenza virus and specifically bind to HA protein of H1 subtype and H5 subtype of influenza viruses, and had a broad-spectrum viral reactivity and ability of neutralizing viruses. Therefore, the antibodies according to the invention are particularly suitable for preventing or treating influenza virus infection or diseases associated with influenza virus infection (e.g., influenza).

Therefore, in one aspect, the invention provides a monoclonal antibody and an antigen binding fragment thereof, wherein the monoclonal antibody can specifically bind to HA1 domain of different HA subtypes of influenza virus and specifically bind to HA1 domain (more particularly, epitopes in HA1 domain) of HA protein of H1 subtype (including seasonal H1N1 and 2009 pandemic H1N1) and H5 subtype of influenza viruses.

In a preferred embodiment, the monoclonal antibody according to the invention has the heavy chain and light chain CDRs selected from the group consisting of:

1) the heavy chain CDR1-3 set forth in SEQ ID NOs: 1-3, and the light chain CDR1-3 set forth in SEQ ID NOs: 4-6;
2) the heavy chain CDR1-3 set forth in SEQ ID NOs: 7-9, and the light chain CDR1-3 set forth in SEQ ID NO: 10-12; and
3) the heavy chain CDR1-3 set forth in SEQ ID NOs: 13-15, and the light chain CDR1-3 set forth in SEQ ID NO: 16-18.

In a preferred embodiment, the monoclonal antibody according to the invention is derived from or is the following monoclonal antibody: the monoclonal antibody produced by hybridoma cell line 12H5 or G10D10 or 8F11, wherein the hybridoma cell line 12H5, G10D10 and 8F11 are deposited in China Center for Type Culture Collection (CCTCC), and have a deposition number of CCTCC NO: C201230, CCTCC NO: C201229 and CCTCC NO: C2013119, respectively.

In a preferred embodiment, the monoclonal antibody or antigen binding fragment thereof according to the invention is selected from Fab, Fab', F(ab')2, Fd, Fv, dAb, complementary determining region fragment, single chain antibody (e.g., scFv), mouse antibody, rabbit antibody, humanized antibody, full-human antibody, chimeric antibody (e.g., human mouse chimeric antibody), or bispecific or poly-specific antibody.

In a preferred embodiment, the monoclonal antibody according to the invention comprises non-CDR region, and the non-CDR region is from species other than murine species, e.g., is from human antibody.

In one aspect, the invention provides a monoclonal antibody and an antigen binding fragment thereof, which can specifically bind to HA1 domain of different HA subtypes of influenza virus and specifically bind to HA1 domain or epitopes comprised therein of HA protein of H1 subtype (including seasonal H1N1 and 2009 pandemic H1N1) and H5 subtype of influenza viruses, wherein the monoclonal antibody can block the binding of the HA1 domain or epitopes comprised therein of the HA protein to a monoclonal antibody selected from the group consisting of:

1) a monoclonal antibody produced by a hybridoma cell line 12H5 with a deposition number of CCTCC NO: C201230;
2) a monoclonal antibody produced by a hybridoma cell line G10D10 with a deposition number of CCTCC NO: C201229; and
3) a monoclonal antibody produced by a hybridoma cell line 8F11 with a deposition number of CCTCC NO: C2013119, by at least 50%, preferably at least 70%, more preferably at least 90%, e.g., at least 95%, at least 96%, at least 97%, at least 98% or at least 99%.

The epitope recognized by such a monoclonal antibody is the same as, or sterically overlaps with, that recognized by the monoclonal antibody 12H5 or G10D10 or 8F11, so that such a monoclonal antibody can reduce the binding of the monoclonal antibody 12H5 or G10D10 or 8F11 to the corresponding epitope by at least 50%, preferably at least 60%, preferably at least 70%, preferably at least 80%, preferably at least 90%, preferably at least 95% or preferably at least 99%.

The invention also provides an isolated nucleic acid molecule, encoding the monoclonal antibody or antigen binding fragment thereof according to the invention. The nucleic acid molecule can be isolated from a hybridoma cell, or can be obtained by genetic engineering recombinant technique or method of chemical synthesis.

In one aspect, the invention provides an isolated nucleic acid molecule, comprising a nucleic acid sequence encoding the heavy chain variable region of the monoclonal antibody according to the invention.

In another aspect, the invention provides an isolated nucleic acid molecule, comprising a nucleic acid sequence encoding the light chain variable region of the monoclonal antibody according to the invention.

In another aspect, the invention provides a vector comprising the isolated nucleic acid molecule according to the invention. The vector according to the invention may be a cloning vector, or an expression vector.

In a preferred embodiment, the vector according to the invention is a plasmid, a cosmid, a phage, etc.

In another aspect, the invention also provides a host cell comprising the isolated nucleic acid molecule or vector according to the invention. Such host cells include, but are not limited to, prokaryotic cell such as *E. coli* cell, and eukaryotic cell such as yeast cell, insect cell, plant cell and animal cell (such as mammalian cell, e.g., mouse cell, human cell, etc.). The cell according to the invention may be a cell line, such as 293T cell.

In another aspect, the invention provides a method for producing the monoclonal antibody or antigen binding fragment thereof according to the invention, comprising culturing the host cell according to the invention under suitable conditions, and recovering the monoclonal antibody or antigen binding fragment thereof according to the invention from the cell culture.

In another aspect, the invention provides a hybridoma cell line 12H5, deposited in China Center for Type Culture Collection (CCTCC), with a deposition number of CCTCC NO: C201230. In another aspect, the invention provides a hybridoma cell line G10D10, deposited in China Center for Type Culture Collection (CCTCC), with a deposition number of CCTCC NO: C201229. In another aspect, the invention provides a hybridoma cell line 8F11, deposited in China Center for Type Culture Collection (CCTCC), with a deposition number of CCTCC NO: C2013119.

The amino acid sequences and/or nucleotide sequences of the heavy chain variable region, the light chain variable region, the heavy chain variable region CDRs and the light chain variable region CDRs can be determined from the monoclonal antibody 12H5, G10D10 and 8F11 by conventional methods.

In another aspect, the invention provides a kit comprising the monoclonal antibody or antigen binding fragment thereof according to the invention. In a preferred embodiment, the monoclonal antibody or antigen binding fragment thereof according to the invention may also comprise a detectable marker. In one preferred embodiment, the kit further comprises a second antibody that specifically binds to the monoclonal antibody or antigen binding fragment thereof according to the invention. Preferably, the second antibody further comprises a detectable marker. Such detectable markers, which are well known by a person skilled in the art, include, but are not limited to, radioisotope, fluorescent substance, luminescent substance, chromophoric substance and enzyme (e.g., horseradish peroxidase), etc.

In another aspect, the invention provides a method for detecting the presence or level of HA protein of H1 subtype and/or H5 subtype influenza virus in a sample, comprising using the monoclonal antibody or antigen binding fragment thereof according to the invention. In one preferred embodiment, the monoclonal antibody or antigen binding fragment thereof according to the invention further comprises a detectable marker. In another preferred embodiment, the method further comprises using a second antibody carrying a detectable marker to detect the monoclonal antibody or antigen binding fragment thereof according to the invention. The method may be used for diagnostic purpose or for non-diagnostic purpose (for example, said sample is a cell sample, rather than a sample from a patient).

In another aspect, the invention provides a method for diagnosing whether a subject is infected by H1 subtype and/or H5 subtype influenza virus comprising: using the monoclonal antibody or antigen binding fragment thereof according to the invention to detect the presence of H1 subtype and/or H5 subtype influenza virus in a sample derived from the subject. In a preferred embodiment, the monoclonal antibody or antigen binding fragment thereof according to the invention further comprises a detectable marker. In another preferred embodiment, the method further comprises using a second antibody carrying a detectable marker to detect the monoclonal antibody or antigen binding fragment thereof according to the invention.

In another aspect, the invention provides use of the monoclonal antibody or antigen binding fragment thereof according to the invention in the manufacture of a kit for detecting the presence or level of HA protein of H1 subtype and/or H5 subtype influenza virus in a sample, or for diagnosing whether a subject is infected by H1 subtype and/or H5 subtype influenza virus.

In another aspect, the invention provides a pharmaceutical composition comprising the monoclonal antibody or antigen binding fragment thereof according to the invention, and a pharmaceutically acceptable carrier and/or excipient.

In another aspect, the invention provides a method for preventing and/or treating infection of H1 subtype and H5 subtype influenza virus and/or a disease caused by the infection (e.g., influenza), comprising administering a prophylactically or therapeutically effective amount of the monoclonal antibody or antigen binding fragment thereof according to the invention or the pharmaceutical composition according to the invention to a subject in need thereof.

In another aspect, the invention provides use of the monoclonal antibody or antigen binding fragment thereof according to the invention in manufacture of a pharmaceutical composition for preventing and/or treating infection of H1 subtype and H5 subtype influenza virus and/or a disease caused by the infection (e.g., influenza).

In another aspect, provided is the monoclonal antibody or antigen binding fragment thereof according to the invention, for use in preventing and/or treating infection of H1 subtype and H5 subtype influenza virus and/or a disease caused by the infection (e.g., influenza).

The medicament and pharmaceutical composition provided in the invention may be used alone or in combination, or may be used in combination with another pharmaceutically active agent (e.g., interferon agents, such as interferon or pegylated interferon).

The embodiments of the invention are described in detail by reference to the drawings and examples. However, a person skilled in the art would understand that the following drawings and examples are intended for illustrating the invention only, rather than defining the scope of the invention. According to the detailed description of the following drawings and preferred embodiments, various purposes and advantages of the invention are apparent for a person skilled in the art.

DESCRIPTION OF DEPOSITION OF BIOLOGICAL MATERIALS

Figure 1:
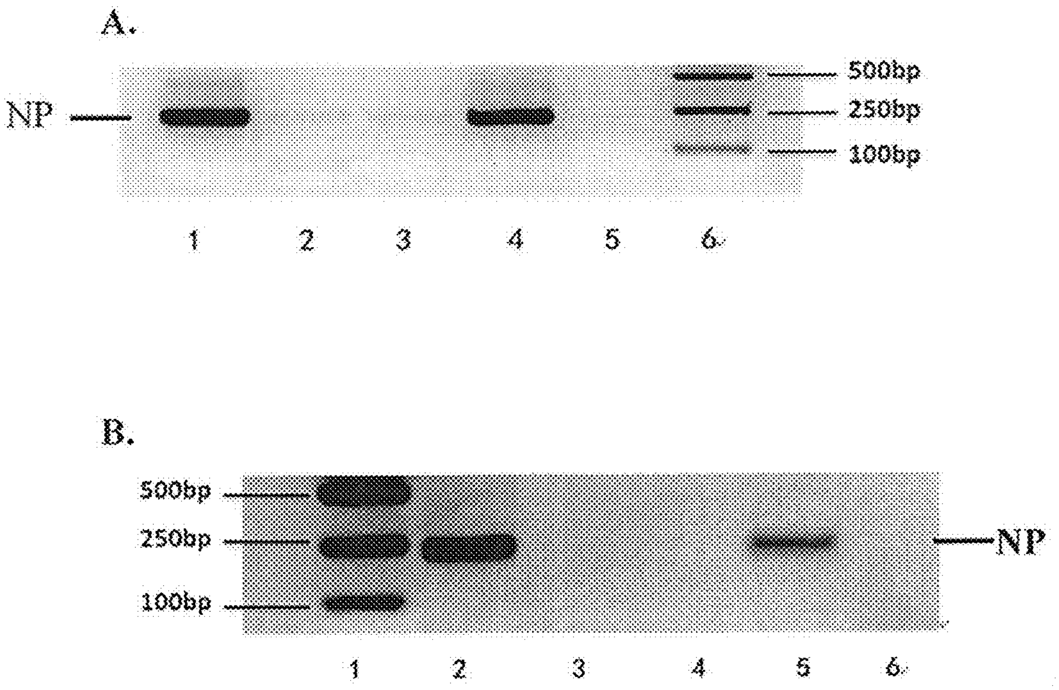
FIG. 1A shows the result of agarose gel electrophoresis, indicating the effect of different samples blocking the monoclonal antibody 12H5 to capture NC20 virus; Lane 1, PBS; Lane 2, 12H5; Lane 3, G10D10; Lane 4, anti-FluB monoclonal antibody 13A12; Lane 5, a control sample free of viral gene; Lane 6, DNA2000 Marker.
FIG. 1B shows the result of agarose gel electrophoresis, indicating the effect of different samples blocking the monoclonal antibody G10D10 to capture NC20 virus; Lane 1, DNA2000 Marker; Lane 2, PBS; Lane 3, 12H5; Lane 4, G10D10; Lane 5, anti-FluB monoclonal antibody 13A12; lane 6, a control sample free of viral gene.

The hybridoma cell lines 12H5 and G10D10 according to invention were deposited in China Center for Type Culture Collection (CCTCC, Wuhan University, Wuhan, China) on Feb. 20, 2012, with a deposition number of CCTCC NO: C201230 and CCTCC NO: C201229, respectively.

Hybridoma cell line SH1-8F11 of the invention (also called hybridoma cell line 8F11 for short in the context), was deposited in China Center for Type Culture Collection (CCTCC, Wuhan University, Wuhan, China) on Sep. 5, 2013, with a deposition number of CCTCC NO: C2013119.

Specific Modes for Carrying Out the Invention

The present invention is illustrated by reference to the following examples (which are not intended to limit the protection scope of the present invention).

Unless indicated otherwise, the molecular biological experimental methods and immunological assays used in the present invention are carried out substantially in accordance with the methods as described in Sambrook J et al., Molecular Cloning: A Laboratory Manual (Second Edition), Cold Spring Harbor Laboratory Press, 1989, and F. M. Ausubel et al., Short Protocols in Molecular Biology, 3rd Edition, John Wiley & Sons, Inc., 1995; restriction enzymes are used under the conditions recommended by manufacturers of the products. When the conditions are not specified in the Examples, the experiments are carried out according to the conventional conditions or the conditions recommended by the manufacturers. The reagents or devices used in the present invention, the manufacturers of which are not indicated, are conventional products in the art that are commercially available. Those skilled in the art understand that the examples are used for illustrating the present invention, but not intended to limit the protection scope of the present invention.

Example 1

Preparation of a Monoclonal Antibody (mAb) Against HA of H1 Subtype Influenza Virus (1) Preparation of Virus:

MDCK cells were inoculated with three seasonal H1N1 influenza virus strains (i.e. A/New Calidonia/20/1999 (H1N1), A/Xiamen/3118/2006 (H1N1), and A/Xiamen/N585/2009 (H1N1)) and a 2009 pandemic H1N1 influenza virus strain A/California/04/2009 (H1N1), respectively. After incubating the cells at 37° C. for 2 days, the supernatant was collected to get the amplified viruses. Live viruses were collected, and were inactivated with 0.03% formalin at 4° C. The inactivated viruses were subjected to HA detection to determine the titer of the inactivated viruses (Note: please refer to WHO Operation Guideline for methods of HA titer determination and HI detection; A/California/04/2009 was given as a gift by Department of Microorganism, University of Hongkong; A/New Calidonia/20/1999, A/Xiamen/3118/2006, A/Xiamen/N585/2009 were the viral strains preserved in the inventor's laboratory).

(2) Experimental Mice:

6-week old female Balb/C mice were provided by Experimental Animal Center, School of Life Sciences, Xiamen University.

(3) Preparation of Hybridoma:

Monoclonal antibodies were obtained by standard in vivo immunization method and PEG fusion method; please refer to Ed Harlow et al., "Antibodies A Laboratory Manual", Cold Spring Harbor Laboratory 1988 for detail. The brief process was as followed.

(4) Immunization of Mice:

The titers of the inactivated viruses were adjusted to a low dose of 8HA for immunization. Firstly, the virus A/New Calidonia/20/1999 (H1N1) was mixed and emulsified with an equal volume of Freund's complete adjuvant (CFA), and then was administered to limbs of mice by multi-point intramuscular injection, at an amount of 400 ul for each mouse. After primary immunization, the viruses A/Xiamen/3118/2006 (H1N1) and A/Xiamen/N585/2009 (H1N1) were separately used in combination with incomplete Freund's adjuvant (IFA) for booster immunization at 14d and 28d. The final booster immunization was carried out to spleens of mice at 42d. The immunogen was a solution of said viruses mixed with an equal volume, 100 ul for each mouse. 3d later, spleens of the mice were taken for fusion experiment.

(5) Cell Fusion:

Firstly, the spleen was ground to obtain a suspension of spleen cells, and then was mixed with mouse myeloma cells SP2/0 in exponential growth phase. Cell fusion was carried out in the presence of PEG1500. The fused cells were re-suspended in 400 ml fusion culture medium, and then were subpackaged to 20 96-well plates for culture. The fusion culture medium was a RPMI1640 complete screening culture medium containing HAT and 20% FBS. Antigenic broad-spectrum clones were screened by ELISA and neutralization assay. After cloning for three times, stable cell lines were obtained.

(6) Screening of Hybridoma:

After culturing the fused cells in the 96-well plates for 10 days, the cell supernatant was taken for Hemagglutination-Inhibition (HI) test. The virus for detection was A/New Calidonia/20/1999 (H1N1), and the positive wells were used for cloning until the antibodies secreted by the cell line were able to stably inhibit the agglutination of virus and red blood cell.

(7) Screening Result of Hybridomas Secreting Monoclonal Antibodies:

25 anti-H1 hemagglutinin monoclonal antibodies including 12H5 were obtained.

(8) Culture of Hybridoma:

25 stable hybridoma cell lines were firstly subjected to amplification culture in a $CO_2$ incubator, and then were transferred from a 96-well plate to a 24-well plate, and later to a 50 ml cell bottle for amplification culture. The cells collected from the cell bottle were injected to peritoneal cavities of mice. 7-10d later, ascites were drawn from the peritoneal cavities of mice.

(9) Purification of Monoclonal Antibody:

The ascites were precipitated with 50% ammonium sulfate. The precipitate was dissolved in PBS, and then purified through Protein A column in AKTA system to get the purified monoclonal antibodies. The purity of the purified monoclonal antibodies was identified by SDS-PAGE.

Example 2

Evaluation of Broad-Spectrum Reactivity of Broad-Spectrum Monoclonal Antibodies Against HA of H1/H5 Subtype by HI Assay Representative stains of seasonal H1N1 influenza virus, representative stains of 2009 pandemic H1N1 influenza A virus, representative stains of highly pathogenic H5N1 avian influenza virus and representative stains of seasonal H3N2 influenza virus, which were isolated at different times from different regions and represented different variant types, were selected. HI assay was used to determine the cross-reactivity of the mAb ascites of said 25 monoclonal antibodies with different H subtype of influenza viruses, and three broad-spectrum monoclonal antibodies 12H5, G10D10 and 8F11, which could recognize H1 and H5 subtype of influenza viruses simultaneously, were identified (Table 1). The monoclonal antibody 12H5 could react with seasonal H1 subtype influenza virus, 2009 pandemic H1N1 influenza A virus and H5 subtype avian influenza virus simultaneously, and showed a good broad-spectrum reactivity with different HA subtypes of influenza virus. The monoclonal antibodies G10D10 and 8F11 could react with seasonal H1 subtype influenza virus and H5 subtype avian influenza virus simultaneously, but not with 2009 pandemic H1N1 influenza A virus. However, the monoclonal antibodies G10D10 and 8F11 had a broader reactive spectrum than 12H5 in the case of seasonal H1 subtype influenza virus, could react with both H1 virus isolated in 1930s and H1 virus newly isolated after 2008, had a broader reactive spectrum than 12H5 in the case of H5 subtype avian influenza virus, and could react with more H5N1 virus strains. The results showed that the monoclonal antibodies G10D10 and 8F11 were also good monoclonal antibodies having broad-spectrum reactivity with different HA subtypes of influenza virus.

TABLE 1

Activity of broad-spectrum monoclonal antibody against HA of H1/H5 subtype in HI assay (HI titer)

| Subtype | Virus | HI titer of mAbs 12H5 | G10D10 | 8F11 |
|---|---|---|---|---|
| Seasonal H1N1 | A/WSN/1933 | ≤100 | 400 | 6400 |
| | A/PR/8/1934 | ≤100 | 400 | 800 |
| | A/Texas/36/1991 | 6400 | ≥12800 | ≥12800 |
| | A/HK/134801/1994 | ≥12800 | ≥12800 | 3200 |
| | A/Beijing/262/1995 | 6400 | ≥12800 | ≥12800 |
| | A/New Calidonia/20/1999 | ≥12800 | ≥12800 | 6400 |
| | A/Shantou/104/2005 | ≥12800 | ≥12800 | ≥12800 |
| | A/Xiamen/3115/2006 | ≥12800 | ≥12800 | ≥12800 |
| | A/Xiamen/1128/2006 | ≥12800 | ≥12800 | ≥12800 |
| | A/Solomon Islands/3/2006 | 800 | ≥12800 | 6400 |
| | A/Brisbane/59/2007 | ≥12800 | ≥12800 | 6400 |
| | A/Xiamen/1152/2008 | ≥12800 | ≥12800 | 3200 |
| | A/Xiamen/N66/2009 | ≤100 | 3200 | 3200 |
| 2009 pandemic H1N1 | A/California/04/2009 | 3200 | ≤100 | ≤100 |
| | A/Xiamen/N514/2009 | 1600 | ≤100 | ≤100 |
| | A/HK/MB-1/2010 | ≥12800 | ≤100 | ≤100 |
| | A/HK/402618/2011 | 3200 | ≤100 | ≤100 |
| H5N1 | Vietnam/1203/2004 | ≤100 | 1600 | 1600 |
| | A/Viet Nam/1194/2004 | ≤100 | 1600 | 1600 |
| | CK/Indonesia/2A/2003 | ≤100 | 3200 | 3200 |
| | Bar-eaded/Qinghai/15C/2005 | 1600 | ≥12800 | ≥12800 |
| | DK/Hunan/101/2004 | ≤100 | ≥12800 | ≥12800 |
| | Ck/HK/YU22/2002 | 1600 | 6400 | 3200 |
| Seasonal H3N2 | A/Brisbane/10/2007 | ≤100 | ≥100 | ≤100 |

Note:
HI titer refers to the maximum dilution fold at which the ascites can completely inhibit HA activity of virus; wherein ≤100 means no reactivity.

Example 3

Evaluation of the Broad-Spectrum Neutralizing Activity (Neutralization Titer) of Broad-Spectrum Monoclonal Antibodies Against HA of H1/H5 Subtype by Microwell Neutralization Assay Neutralization activity is an important index for assessing whether a monoclonal antibody has therapeutic potential. Microwell neutralization assay was used to determine the neutralization activity of the monoclonal antibodies 12H5, G10D10 and 8F11 for representative strains of H1N1 and H5N1 subtype influenza viruses (Hulse-Post et al., PNAS. 2005, 102: 10682-7). The results (Table 2) showed that the results of neutralization assay were substantively consistent with the results of HI assay, and the three monoclonal antibodies (12H5, G10D10 and 8F11) had broad-spectrum cross-neutralizing activity with H1N1 and H5N1 viruses.

TABLE 2

Activity of broad-spectrum monoclonal antibodies against HA of H1/H5 subtype in neutralization assay

| Virus | subtype/clade | Neutralizing titer 12H5 | G10D10 | 8F11 |
|---|---|---|---|---|
| A/HK/134801/1994 | seasonal H1N1 | 12800 | 12800 | 12800 |
| A/New Calidonia/20/1999 | seasonal H1N1 | 12800 | 12800 | 12800 |
| A/Brisbane/59/2007 | seasonal H1N1 | 3200 | 12800 | 12800 |
| A/California/07/2009 | 2009 pandemic H1N1 | 1600 | ≤100 | ≤100 |
| A/Xiamen/N514/2009 | 2009 pandemic H1N1 | 1600 | ≤100 | ≤100 |
| A/HK/MB-1/2010 | 2009 pandemic H1N1 | 12800 | ≤100 | ≤100 |
| A/HK/402618/2011 | 2009 pandemic H1N1 | 3200 | ≤100 | ≤100 |
| A/Viet Nam/1194/2004 | H5N1 (clade 1) | 3200 | 6400 | 12800 |
| A/BHGs/Qinghai/15C/2005 | H5N1 (clade 2) | 1600 | 1600 | 3200 |
| A/Ck/HK/YU22/2002 | H5N1 (clade 8) | 1600 | 12800 | 12800 |
| A/Brisbane/10/2007 | H3N2 | ≤100 | ≤100 | ≤100 |

≤100, means no reactivity.

Example 4

Evaluation of Broad-Spectrum Monoclonal Antibody Against HA of H1/H5 Subtype by Blocking-Capturing PCR Method In order to determine the recognition specificity of broad-spectrum monoclonal antibody, broad-spectrum monoclonal antibody was assayed by blocking-capturing PCR method. The method was as followed:

1. Materials and Methods (1) Ultracentrifugation of Influenza Virus:

A given amount of seasonal H1N1 influenza virus strain A/New Calidonia/20/1999 (H1N1) was inactivated with 0.03% formalin at 4° C. The inactivated virus was subjected to sucrose density gradient centrifugation in Ultracentrifuge at 4° C., 25200 rpm for 3 hours. The virus precipitate was dissolved with 1×PBS at 4° C. overnight. The ultracentrifuged virus was subjected to HA detection to determine the titer of the virus solution.

(2) Monoclonal Antibodies:

broad-spectrum H1 monoclonal antibodies (12H5 and G10D10), unrelated control monoclonal antibody (a monoclonal antibody against HA of type B influenza virus, i.e. anti-Flu B HA mAb 13A12, which cannot bind to H1 subtype of influenza virus A A/New Calidonia/20/1999); the concentration of monoclonal antibody was 0.5 mg/ml.

```
(3) NP primers:
upstream primer q-NP-F (SEQ ID NO: 27):
5'-AGT TGG AAC AAT GGT GAT GG-3'

downstream primer q-NP-R (SEQ ID NO: 28):
5'-TTC CGG CTC TCT CTC ACT TGA TC-3'
```

(4) Blocking-Capturing PCR Assay:

The monoclonal antibody to be blocked (the coated monoclonal antibody) was pre-coated on polystyrene plate. The blocking monoclonal antibody (the monoclonal antibody to be tested) was mixed with an equal volume of ultracentrifuged virus and incubated at 37° C. for 1 hour, and then added to the plate pre-coated with monoclonal antibody. After carrying out the reaction at 37° C. for 2 hours, the unbound virus was washed off with conventional washing solution (PBST) for ELISA, and the total RNA of the influenza virus captured on the plate was then extracted by Automated Nucleic Acid Extractor. After reverse transcription of the RNA into cDNA, influenza virus NP gene-specific primer was used for PCR. After 28 cycles of amplification, the PCR amplification product was subjected to agarose gel electrophoresis to determine the ability of the monoclonal antibody to be tested to block the capturing of virus by the coated monoclonal antibody. The more the monoclonal antibody to be tested is similar to the coated monoclonal antibody with respect to the recognition epitope, the higher its blocking ability is, the less the virus captured by the coated monoclonal antibody is, and the weaker the signal of the PCR product determined by electrophoresis is. Quantity One software was finally used to analyze the signal of PCR products quantitatively, and by comparing the fluorescent signal values of the monoclonal antibody to be tested and the unrelated control monoclonal antibody, the mutual blocking rate of the monoclonal antibody to be tested and the coated monoclonal antibody was calculated.

2. Results and Analysis

Blocking-capturing PCR method and Quantity One software were used to analyze and determine the blocking rate of PBS, 12H5, G10D10 and 13A12 to block the capture of H1 influenza virus NC20 by monoclonal antibody 12H5, respectively. The results (FIG. 1A) showed that H1 monoclonal antibodies 12H5 and G10D10 could well block the capture of NC20 virus by the monoclonal antibody 12H5, while neither of the unrelated monoclonal antibody 13A12 and PBS control could block the capture of NC20 by the monoclonal antibody 12H5. After scanning quantitative analysis by Quantity One software, it was determined that in FIG. 1A, the PeaK int×mm value was 1557.323 for Lane 1, 122.286 for Lane 2, 125.807 for Lane 3, 1413.796 for Lane 4, and it was calculated that the corresponding blocking rate was 92.14% for 12H5 vs. 12H5, 91.92% for G10D10 vs. 12H5, 9.22% for FluB unrelated monoclonal antibody 13A12 vs. 121-15.

By the same method, the blocking rate of PBS, 12H5, G10D10 and FluB-unrelated monoclonal antibody 13A12 to block the capture of H1 influenza virus NC20 by the monoclonal antibody G10D10 were determined. The results (FIG. 1B) showed that H1 monoclonal antibody 12H5 and G10D10 could well block the capture of NC20 virus by the monoclonal antibody G10D10, and neither of the unrelated monoclonal antibody 13A12 and PBS control could block the capture of NC20 by the monoclonal antibody 12H5. After scanning quantitative analysis by Quantity One software, it was determined that in FIG. 1B, the PeaK int×mm value was 1052.753 for Lane 1, 65.227 for Lane 2, 20.841 for Lane 3, and 923.302 for Lane 4, and it was calculated that the corresponding blocking rate was 93.80% for 12H5 vs. G10D10, 98.02% for G10D10 vs. G10D10, and 12.30% for FluB-unrelated monoclonal antibody 13A12 vs. G10D10.

The results showed that the broad-spectrum monoclonal antibodies 12H5 and G10D10 were very similar to each other with respect to the recognition epitope, and therefore 12H5 and G10D10 could block each other to a large extent.

Example 5

The Epitope Recognized by Broad-Spectrum Monoclonal Antibodies Against HA of H1/H5 Subtype was Determined as within HA1 Domain by Analyzing Escape Mutation The monoclonal antibodies 12H5, G10D10 and 8F11 were used to induce and screen escape mutants. The positive escape virus thus obtained was purified and subjected to amplification culture, and its gene was obtained, sequenced and was analyzed for the escape mutation site, so as to determine the region in which the epitope recognized by the monoclonal antibodies 12H5, G10D10 and 8F11 was present.

1. Materials and Methods:

Parent virus: seasonal H1N1 virus A/Brisbane/59/2007 and 2009 pandemic H1N1 virus A/California/07/2009 were selected as parent viruses for escape mutation screening.

Monoclonal antibodies: 12H5, G10D10 and 8F11

Escape screening: $10^5$ TCID50 virus was mixed with a monoclonal antibody, and the final concentration of monoclonal antibody was 1 mg/ml, with a total volume of 1 ml. After incubating at room temperature for 4 hours, the virus-monoclonal antibody complex was used for infecting the MDCK cells pre-plated on a 96-well plate. After incubating the mixture of the virus and monoclonal antibody with the cells for 2 hours, the mixture was taken, and a maintenance medium containing 50 ug/ml monoclonal antibody was added, and the cells were cultured at 37° C. for 48 h. The culture supernatant was determined by hemagglutination test, the positive virus wells were cloned. After cloning for three times, stable escape viral strains were obtained.

Localization of escape mutation sites: the obtained escape mutant virus was subjected to RT-PCR for amplification of the structural gene of the virus, and the structural gene thus obtained was sequenced and was aligned with the structural gene of the parent virus to obtain the escape mutation sites.

2. Results and Analysis

The results of escape mutation showed that all the escape mutation sites were present in the gene encoding HA1 domain of influenza virus HA protein.

In particular, the escape mutation screening results for the monoclonal antibody 12H5 (Table 3) showed that the escape mutation sites involved the amino acid residues at position 138, 142 and 186 (H3 numbering, the same below) of HA1 gene. 5 escape strains were obtained by A/Brisbane/59/2007 (H1N1)-based virus escape screening, and all had mutation at position 142 of HA (N142D); 19 escape strains were obtained by A/California/07/2009 (2009 pandemic H1N1)-based virus escape screening, among which 1 had mutation at position 138 of HA (A138S), 8 had mutation at position 142 of HA (A142E), and the remaining 10 had mutation at position 186 of HA (S186P).

TABLE 3

The amino acid mutation sites of HA from the monoclonal antibody 12H5-induced escape strains

| H1N1 parent virus | escape mutation site in HA [a] |
|---|---|
| A/Brisbane/59/2007 | N142D(5/5) |
| A/California/07/2009 | A138S(1/19) |
| | A142E(8/19) |
| | S186P(10/19) |

The escape mutation screening result for the monoclonal antibody G10D10 (Table 4) showed that the escape mutation site involved the amino acid residue at position 142 of HA1 gene. 4 escape strains were obtained by A/Brisbane/59/2007 (H1N1)-based virus escape screening, and all had mutation at position 142 (N142H for two strains, N142S for one strain and N142Y for one strain).

TABLE 4

| The amino acid mutation sites of HA from the monoclonal antibody G10D10-induced escape strains | |
|---|---|
| H1N1 parent virus | escape mutation site in HA [a] |
| A/Brisbane/59/2007 | N142H(2/4)<br>N142S(1/4)<br>N142Y(1/4) |

The escape mutation screening result for the monoclonal antibody 8F11 (Table 5) showed that the escape mutation site involved the amino acid residue at position 142 of HA1 gene. 5 escape strains were obtained by A/Brisbane/59/2007 (H1N1)-based virus escape screening, and all had mutation at position 142 (N142D for 4 strains, and N142K for one strain).

TABLE 5

| The amino acid mutation sites of HA from the monoclonal antibody 8F11-induced escape strains | |
|---|---|
| H1N1 escape parent virus | escape mutation site in HA [a] |
| A/Brisbane/59/2007 | N142D(4/5)<br>N142K(1/5) |

The escape mutation results showed that the monoclonal antibodies 12H5, G10D10, and 8F11 recognized similar epitopes, and the epitopes they recognized were all present in HA1 domain of influenza virus HA protein, and all of them recognized the amino acid at position 142 of HA.

Example 6

Separation of Light Chain Gene and Heavy Chain Gene of Monoclonal Antibodies Against HA of H1/H5 Subtype About $10^7$ hybridoma cells were cultured by means of semi-adherence, and the adhered cells were suspended by blowing. The suspension was transferred to a new 4 ml centrifuge tube, and centrifuged at 1500 rpm for 3 min. The cell precipitate was collected and re-suspended in 100 μl sterile PBS (pH=7.45), and then transferred to a new 1.5 ml centrifuge tube. 800 μl Trizol (Roche, Germany) was added, mixed gently by reverse mixing, and then standing for 10 min. 200 μl chloroform was added, shaken vigorously for 15 s, standing for 10 min, and centrifuged at 4° C., 12000 rpm for 15 min. The supernatant liquid was transferred to a new 1.5 ml centrifuge tube, and an equal volume of isopropanol was added, mixed, standing for 10 min, and then centrifuged at 4° C., 12000 rpm for 10 min. The supernatant was removed, 600 μl of 75% ethanol was added for washing, and then centrifuged at 4° C., 12000 rpm for 5 min. The supernatant was removed, and the precipitate was dried under vacuum at 60° C. for 5 min. The transparent precipitate was dissolved in 70 ul DEPC $H_2O$, and was subpackaged into two tubes. To each tube, 1 μl reverse transcription primer was added, wherein the reverse transcription primer added to one tube was MVJkR (5'-CCG TTT GKA TYT CCA GCT TGG TSC C-3') (SEQ ID NO: 19), for amplification of the gene of light chain variable region, and the reverse transcription primer added to the other tube was MVDJhR (5'-CGG TGA CCG WGG TBC CTT GRC CCC A-3') (SEQ ID NO: 20), for amplification of the gene of heavy chain variable region. To each tube, 1 μl dNTP (Sangon Biotech (Shanghai) Co., Ltd.) was added, and the tubes were placed in 72° C. water bath for 10 min and then immediately in an ice bath for 5 min. 10 μl 5× reverse transcription buffer, 1 μl AMV (10 u/ul, Pormega), and 1 μl Rnasin (40 u/μl, Promega) were added. After mixing the mixture well, RNA was reverse transcripted into cDNA at 42° C.

The gene of the variable region of the antibody was isolated by polymerase chain reaction (PCR) method. The primer set synthesized according to Ig-Prime kits of Novagen Company and another two designed and synthesized downstream primers MVJkR, MVDJhR (synthesized by ShangHai Boya Company) were used, wherein MVJkR was a downstream primer for amplification of the gene of light variable region, and MVDJhR was a downstream primer for amplification of the gene of heavy variable region. The templates were the two cDNA as synthesized above. PCR conditions were: 94° C. 5 min; (94° C. 40 s, 53° C. 1 min, 72° C. 50 s)×35 cycles; 72° C. 15 min. The fragments of interest were recovered and were cloned to pMD 18-T vector, and then were sent to ShangHai Boya Company for sequencing. By blast alignment, the sequences of antibody variable regions were determined, and the corresponding amino acid sequences were determined.

By the above method, the genes of the antibody variable regions were cloned from the hybridoma cell lines secreting broad-spectrum monoclonal antibodies 12H5, G10D10 and 8F11, and the corresponding amino acid sequences were determined. Table 6 showed the sequences of the upstream primers used, and Table 7 showed the amino acid sequences of antibody variable regions, and the complementary determinant regions (CDRs) were determined by Kabat method (Kabat E A, Wu T T, Perry H M, Gottesman K S, Coeller K. Sequences of proteins of immunological interest, U.S Department of Health and Human Services, PHS, NIH, Bethesda, 1991).

TABLE 6

Sequences of upstream primers for amplification of variable region genes of the broad-spectrum monoclonal antibodies 12H5, G10D10, and 8F11

| Variable region gene of mAb | Name of upstream primer | Sequence of upstream primer |
|---|---|---|
| 12H5Vh | MuIgVh5'-D1 (SEQ ID NO: 21) | 5'-ATGGRCAGRCTTA CWTYYTCATTCCT-3' |
| 12H5Vk | MuIgkV15'-E1 (SEQ ID NO: 22) | 5'-ATGTGGGGAYCGK TTTYAMMCTTTTCAAT TG-3' |
| G10D10Vh | MuIgVh5'-C2 (SEQ ID NO: 23) | 5'-ATGGVTTGGSTGT GGAMCTTGCYATTCC T-3' |
| G10D10Vk | MuIgkV15'-B (SEQ ID NO: 24) | 5'-ATGGAGACAGACA CACTCCTGCTAT-3' |
| 8F11Vh | MuIgVh5'-C2 (SEQ ID NO: 25) | 5'-AtGGVTTGGSTGT GGAMCTTGCYATTCC T-3' |
| 8F11Vk | MuIgkV15'-G2 (SEQ ID NO: 26) | 5'-ATGGTYCTYATVT CCTTGCTGTTCTG G-3' |

TABLE 7

Amino acid sequences of CDRs of 3 monoclonal antibodies against HA of H1/H5 subtype as identified by Kabat method

| Antibody chain | CDR No. | Sequences of CDRs of broad-spectrum mAb against H1/H5 subtype 12H5 | G10D10 | 8F11 |
|---|---|---|---|---|
| Heavy chain | CDR1 | GYTFTKNG (SEQ ID NO: 1) | GYTFTKYG (SEQ ID NO: 7) | GYTFTNYG (SEQ ID NO: 13) |
| | CDR2 | INTYTGEP (SEQ ID NO: 2) | INTYTGEP (SEQ ID NO: 8) | INTYSGEP (SEQ ID NO: 14) |
| | CDR3 | ARMVRDAMDF (SEQ ID NO: 3) | ARMGRDAMDY (SEQ ID NO: 9) | ASLRRDAMDH (SEQ ID NO: 15) |
| Light chain | CDR1 | QSVDFDGYNY (SEQ ID NO: 4) | QSVDFDGYIY (SEQ ID NO: 10) | HSVDFDGYVY (SEQ ID NO: 16) |
| | CDR2 | AAS (SEQ ID NO: 5) | AAS (SEQ ID NO: 11) | AAS (SEQ ID NO: 17) |
| | CDR3 | QQSNEDPYT (SEQ ID NO: 6) | QQSREDPWT (SEQ ID NO: 12) | QQSREDPWT (SEQ ID NO: 18) |

Example 7

Figure 2:
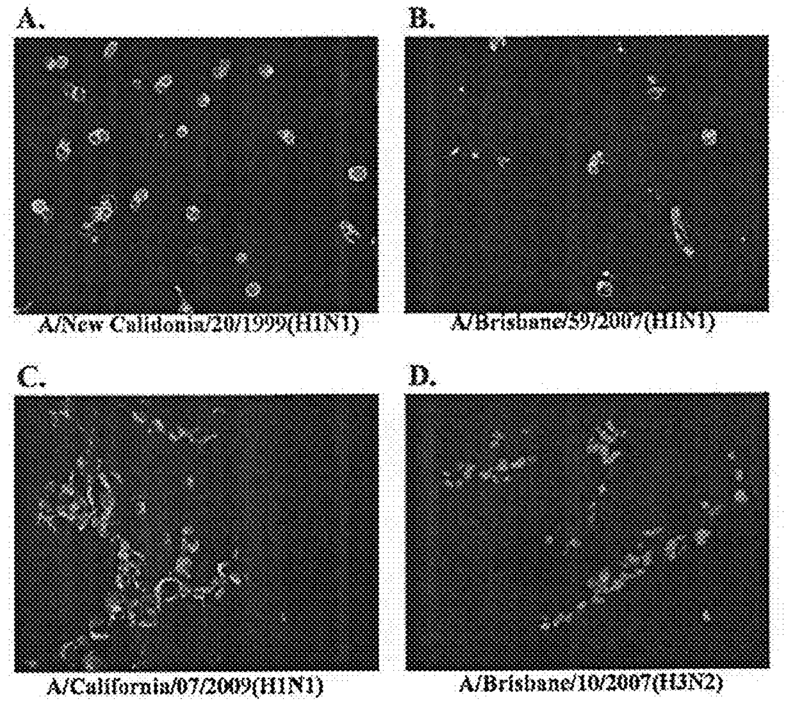
FIG. 2 shows the effect of the monoclonal antibody 12H5 for the detection of influenza virus antigen in cells.
Figure 3:
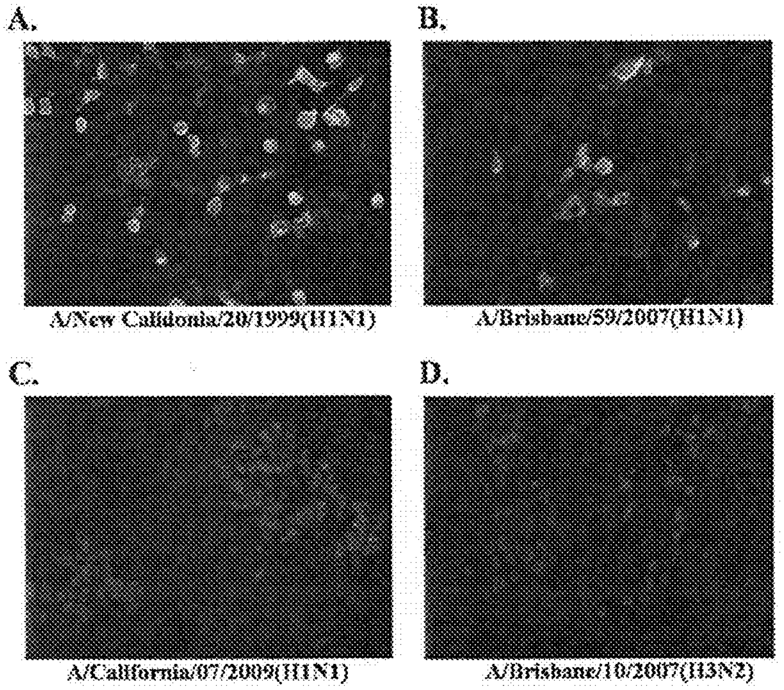
FIG. 3 shows the effect of the monoclonal antibody G10D10 for the detection of influenza virus antigen in cells.

Application of Broad-Spectrum Monoclonal Antibodies Against HA of H1/H5 Subtype for Detection of Influenza Virus To determine the effect of said broad-spectrum monoclonal antibodies against HA of H1/H5 subtype for detection of influenza virus, 12H5 and G10D10 were used as representative monoclonal antibodies for the experiment. MDCK cells were infected by representative strains of seasonal H1 subtype influenza virus (A/New Calidonia/20/1999 and A/Brisbane/59/2007), a representative strain of 2009 pandemic H1N1 influenza A virus (A/California/04/2009), and a representative strain of seasonal H3 subtype influenza virus (A/Brisbane/59/2007 (H3N2)) as control. The cells were fixed 24 h after infection. Immunofluorescence assay was used to analyze the effect of monoclonal antibodies 12H5 and G10D10 for detection of influenza virus. The results (FIG. 2) showed that the monoclonal antibody 12H5 had good reactivity with the HA antigens of the two classes of H1 subtype influenza viruses, wherein the fluorescence was mainly observed on cell membrane, and was also observed in cytoplasm. The monoclonal antibody 12H5 had no specific reactivity with H3 subtype influenza virus and negative cells. The monoclonal antibody G10D10 had good reactivity with the HA antigens of the seasonal H1N1 influenza virus, but had no specific reactivity with the 2009 pandemic H1N1 influenza A virus and H3 subtype influenza virus (FIG. 3). The results were consistent with the results of HI test and the neutralization assay, indicating that they are useful for detecting influenza virus in cells.

Example 8

Application of Broad-Spectrum Monoclonal Antibodies Against HA of H1/H5 Subtype for Treatment of Influenza Virus Infection Passive immunotherapy of infectious diseases with antibodies is a potentially effective route for anti-viral treatment. It was demonstrated by in vitro neutralization assay in microwells that the monoclonal antibodies of the invention had high neutralizing activity against H1N1 and H5N1 virus strains isolated from different regions at different times, the monoclonal antibodies were characterized by broad-spectrum H1 neutralizing reactivity, high neutralizing titer, and a good neutralizing effect for some H5. To further demonstrate the anti-viral effect of the monoclonal antibodies in vivo, the in vivo experiment on the anti-viral treatment of H1N1 and H5N1 influenza virus with the monoclonal antibodies was carried out in an Animal Biosafety Level (ABSL)-3 laboratory, based on H1N1 and H5N1 virus-infected animal models, Balb/C mice. The experiment was as followed.

(1) Materials and Methods

Animal: Balb/C mice, SPF, 6-8 week old, female, weighted about 20 g.

Monoclonal antibody: 12H5 and G10D10.

H1N1 virus:

Seasonal H1N1 influenza virus strain A/PuertoRico/8/1934 (H1N1), called PR8 for short;

A/California/07/2009 (H1N1)-MA, a mouse adaptive strain of 2009 pandemic H1N1 influenza A virus stain A/California/07/2009 (H1N1), called CA07-MA for short;

H5N1 virus: A/Bar-Head Gs/QH/15C/2005 (H5N1), called QH15C for short.

Anesthetic: Isoflorane

Animal grouping: mice were sent to ABSL-3 laboratory one day ahead, and were divided into 4 groups, with 5 mice per cage, designated as G1, G2, . . . etc.; the weight of each mouse was recorded, the regimens were shown in Table 8.

Virus infection: H5 virus QH15C was pre-diluted to $10^3$ $TCID_{50}/\mu l$, H1 viruses RP8 and CA04-MA were pre-diluted to $10^5$ $TCID_{50}/\mu l$, the mice were inoculated with the virus at 25 μl/mouse. Before inoculation, mice were anesthetized with isoflorane, and then infected by inoculation of virus via nasal cavity.

MAb intervention: 24 h (dpi.1) after virus infection, the mice in antibody-treatment group were injected with antibody at different doses, i.e. 20 mg/kg, 10 mg/kg, 5 mg/kg and 2.5 mg/kg, respectively, wherein the injection volume was 100 μl/mouse.

Observation: 1-14 days after virus infection, weight, survival, and the corresponding behavioral symptoms of mice were recorded every day.

TABLE 8

Regimen of anti-viral treatment with broad-spectrum monoclonal antibody

| Group | Note | Infectious virus | mAb intervention | Number of mice |
|---|---|---|---|---|
| 12H5 treatment regimen | | | | |
| G1 | Blank control group | PBS | PBS | 5 |
| G2 | H1 virus control group | CA07-MA | PBS | 5 |

TABLE 8-continued

| Group | Note | Infectious virus | mAb intervention | Number of mice |
|---|---|---|---|---|
| Regimen of anti-viral treatment with broad-spectrum monoclonal antibody | | | | |
| G3 | H1 treatment group 1 | CA07-MA | 12H5 10 mg/kg | 5 |
| G4 | H1 treatment group 2 | CA07-MA | 12H5 5 mg/kg | 5 |
| G5 | H1 treatment group 3 | CA07-MA | 12H5 2.5 mg/kg | 5 |
| G6 | H5 virus control group | QH15C | PBS | 5 |
| G7 | H5 treatment group 1 | QH15C | 12H5 10 mg/kg | 5 |
| G8 | H5 treatment group 2 | QH15C | 12H5 5 mg/kg | 5 |
| G9 | H5 treatment group 3 | QH15C | 12H5 2.5 mg/kg | 5 |
| G10D10 treatment regimen | | | | |
| G10 | Blank control group | PBS | PBS | 5 |
| G11 | H1 virus control group | PR8 | PBS | 5 |
| G12 | H1 treatment group | PR8 | G10D10 20 mg/kg | 5 |
| G13 | H5 virus control group | QH15C | PBS | 5 |
| G14 | H5 treatment group 1 | QH15C | 12H5 10 mg/kg | 5 |
| G15 | H5 treatment group 2 | QH15C | 12H5 5 mg/kg | 5 |
| G16 | H5 treatment group 3 | QH15C | 12H5 2.5 mg/kg | 5 |

(2) Results and Analysis

Figure 4:
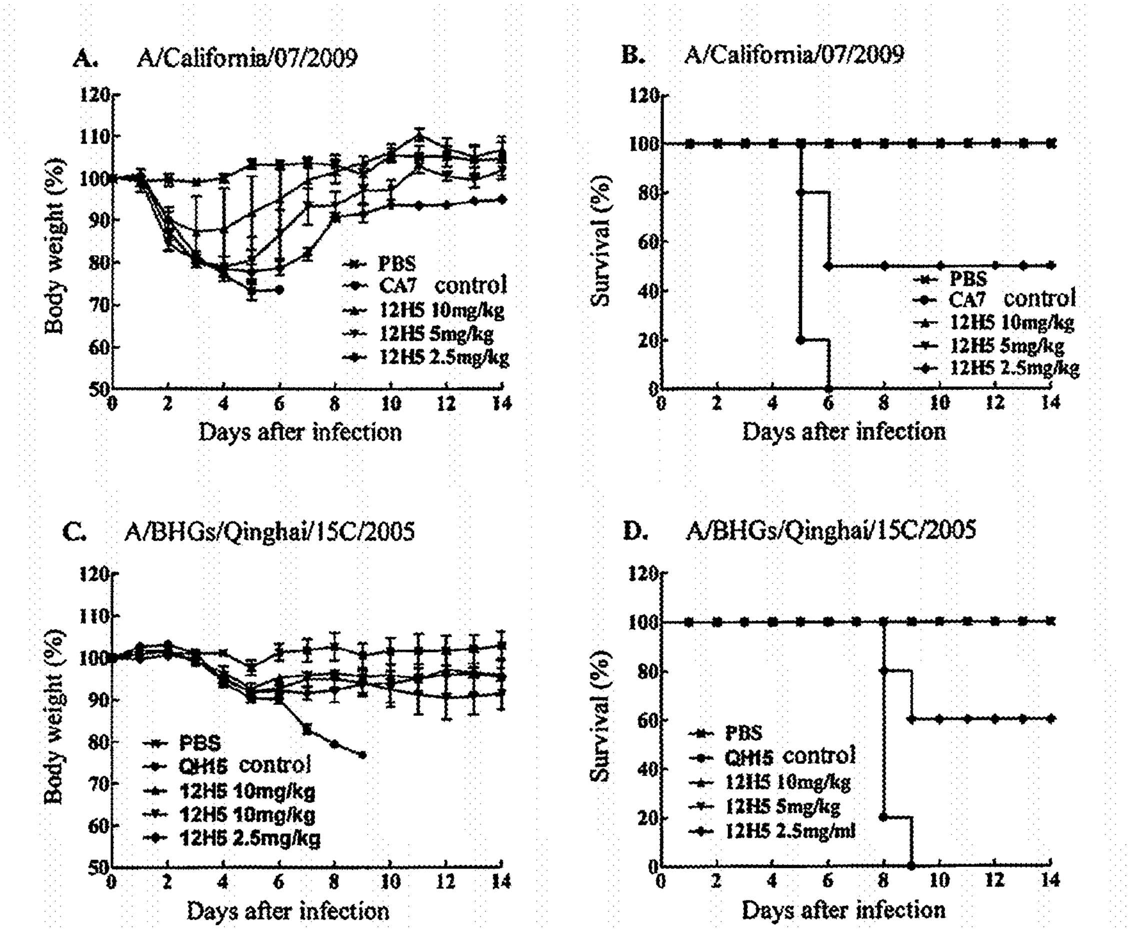
FIG. 4 shows the protective effect of the monoclonal antibody 12H5 for the treatment of mice infected by influenza virus.

Mice were separately infected by CA7 virus of 2009 pandemic H1N1 and H5N1 virus strain QH15C at a one-week lethal dose. Antibody intervention was initiated 1 day after infection. The treatment effect of monoclonal antibody was determined by measuring the body weight and calculating the survival rate (FIG. 4). It could be seen that no significant weight fluctuation was observed in negative control group during the experiment; significant weight loss was observed in two virus control groups, all the mice died 6 days after infection in CA07 virus control group, and all the mice died 9 days after infection in QH15C virus control group. In the case of said two viruses, 12H5 antibody intervention at different doses leaded to weight recovery in mice (FIGS. 4A and 4C). It could be found by observing the survival of mice during 1-14 days after virus infection that the treatment with 12H5 monoclonal antibody at a dose of 10 mg/kg and 5 mg/kg could enable the mice infected by said two viruses survive normally for 14 days, and the treatment effect reached 100%, whereas 12H5 at a dose of 2.5 mg/kg could not completely protect the mice and the treatment effect was 60% for said two viruses (FIGS. 4B and 4D). The results showed that 12H5 also had a good protective effect at a low dose (5 mg/Kg).

Figure 5:
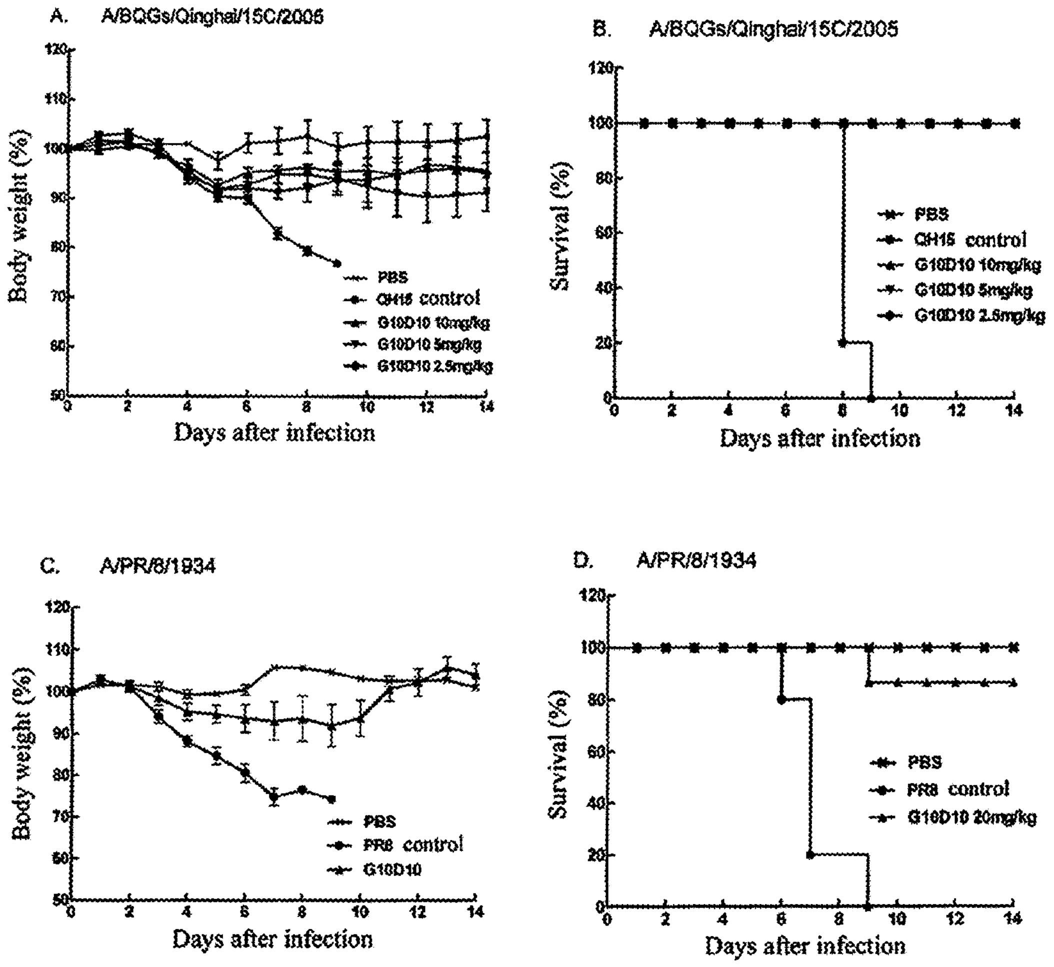
FIG. 5 shows the protective effect of the monoclonal antibody G10D10 for the treatment of mice infected by influenza virus.

Mice were separately infected by H5N1 virus strain QH15C and seasonal influenza virus strain PR8 (recent seasonal H1N1 virus was not pathogenic to mice, and therefore early H1N1 virus strain PR8 pathogenic to mice was used in this experiment) at a one-week lethal dose, and used for evaluating the treatment effect of the monoclonal antibody G10D10. Since the monoclonal antibody G10D10 had a weak activity for PR8 (HI titer was only 400), a high dose (20 mg/kg) was used in the animal experiment. The results (FIG. 5) showed that the monoclonal antibody G10D10 had a better therapeutic effect than the monoclonal antibody 12H5 in the case of H5 virus, wherein the mice could regain weight when treated with the antibody at any of the three doses (FIG. 5A), and the survival of mice was 100% (FIG. 5B). In the case of PR8 virus, G10D10 monoclonal antibody intervention at a dose of 20 mg/kg could also effectively relieve weight loss in mice (FIG. 5C), and finally make 80% of mice survive (FIG. 5D), indicating that the monoclonal antibody G10D10 also had a broad-spectrum anti-viral therapeutic effect.

Although the specific embodiments of the invention have been described in detail, those skilled in the art would understand that, according to all the disclosed teachings, various modifications and changes can be made, and that such modifications and changes are within the scope of the present invention. The scope of the present invention is given by the appended claims and any equivalents thereof.

The invention claimed is:

1. A monoclonal antibody or an antigen binding fragment thereof, which can specifically bind to HA1 domain of different HA subtypes of influenza virus and specifically bind to HA1 domain of HA protein of H1 subtype and H5 subtype of influenza viruses, wherein the monoclonal antibody has the heavy chain and light chain CDRs selected from the group consisting of:

1) the heavy chain CDR1-3 set forth in SEQ ID NOs: 1-3, and the light chain CDR1-3 set forth in SEQ ID NOs: 4-6;

2) the heavy chain CDR1-3 set forth in SEQ ID NOs: 7-9, and the light chain CDR1-3 set forth in SEQ ID NO: 10-12; and 3) the heavy chain CDR1-3 set forth in SEQ ID NOs: 13-15, and the light chain CDR1-3 set forth in SEQ ID NO: 16-18.

2. An isolated nucleic acid molecule, encoding the monoclonal antibody or antigen binding fragment thereof according to claim 1.

3. A vector, comprising the isolated nucleic acid molecule according to claim 2.

4. A host cell, comprising the isolated nucleic acid molecule according to claim 2 or a vector comprising the isolated nucleic acid molecule.

5. A hybridoma cell line, which is selected from the group consisting of:

1) a hybridoma cell line 12H5, deposited in China Center for Type Culture Collection (CCTCC), with a deposition number of CCTCC NO: C201230;

2) a hybridoma cell line G10D10, deposited in China Center for Type Culture Collection (CCTCC), with a deposition number of CCTCC NO: C201229; and 3) a hybridoma cell line 8F11, deposited in China Center for Type Culture Collection (CCTCC), with a deposition number of CCTCC NO: C2013119.

6. A pharmaceutical composition, comprising the monoclonal antibody or antigen binding fragment thereof according to claim 1, and a pharmaceutically acceptable carrier and/or excipient.

7. A pharmaceutical composition, comprising the isolated nucleic acid molecule according to claim 2 or a vector comprising the isolated nucleic acid molecule, and a pharmaceutically acceptable carrier and/or excipient.

8. A method for producing the monoclonal antibody or antigen binding fragment thereof according to claim 1, comprising 1) expressing an isolated nucleic acid molecule encoding the monoclonal antibody or antigen binding fragment thereof in a host cell, to produce the monoclonal antibody or antigen binding fragment thereof; and 2) isolating the monoclonal antibody or antigen binding fragment thereof.

9. The monoclonal antibody or antigen binding fragment thereof produced by the method according to claim 8.

10. A method for detecting the presence or level of HA protein of H1 subtype and/or H5 subtype influenza virus in a sample, comprising contacting the monoclonal antibody or antigen binding fragment thereof according to claim 1 with a sample having or suspected to have HA protein of H1 subtype influenza virus, and (2) detecting any binding between the monoclonal antibody or antigen binding fragment thereof and HA protein of H1 subtype influenza virus.

11. A method for diagnosing whether a subject is infected by H1 subtype and/or H5 subtype influenza virus, comprising, comprising (1) contacting the monoclonal antibody or antigen binding fragment thereof according to claim 1 with a sample from a subject that is suspected to be infected by H1 subtype and/or H5 subtype influenza virus, and (2) detecting the presence of H1 subtype and/or H5 subtype influenza virus in the sample by detecting any binding between the monoclonal antibody or antigen binding fragment thereof and HA protein of H11 subtype and/or H5 subtype influenza virus.

12. A method for preventing and/or treating infection of H1 subtype and H5 subtype influenza virus or a disease caused by influenza virus, comprising administering a prophylactically or therapeutically effective amount of the monoclonal antibody or antigen binding fragment thereof according to claim 1 to a subject in need thereof.

13. The monoclonal antibody or antigen binding fragment thereof according to claim 1, wherein the monoclonal antibody has one or more of the following features:

(1) the monoclonal antibody is derived from or is the following monoclonal antibody: the monoclonal antibody produced by hybridoma cell line 12H5 or G10D10 or 8F11, wherein the hybridoma cell lines 12H5, G10D10 and 8F11 are deposited in China Center for Type Culture Collection (CCTCC), and have a deposition number of CCTCC NO: C201230, CCTCC NO: C201229 and CCTCC NO: C2013119, respectively;

(2) the monoclonal antibody or antigen binding fragment thereof is selected from Fab, Fab', F(ab')2, Fd, Fv, dAb, complementary determining region fragment, single chain antibody, mouse antibody, humanized antibody, chimeric antibody, or bispecific or poly-specific antibody; and (3) the monoclonal antibody comprises non-CDR region, and the non-CDR region is from species other than murine species.

14. The pharmaceutical composition according to claim 6, wherein the pharmaceutical composition is a vaccine.

15. The monoclonal antibody or antigen binding fragment thereof according to claim 13, wherein the single chain antibody is scFv.

16. The monoclonal antibody or antigen binding fragment thereof according to claim 13, wherein the chimeric antibody is a human mouse chimeric antibody.

17. The monoclonal antibody or antigen binding fragment thereof according to claim 13, wherein the non-CDR region is from a human antibody.

18. The monoclonal antibody or an antigen binding fragment thereof according to claim 1, which can specifically bind to HA1 domain of HA protein of seasonal H1N1 subtype and H5 subtype of influenza viruses.

19. The monoclonal antibody or an antigen binding fragment thereof according to claim 1, which can specifically bind to HA1 domain of HA protein of 2009 pandemic H1N1 subtype and H5 subtype of influenza viruses.

* * * * *

SEQUENCE LISTING

<160> NUMBER OF SEQ ID NOS: 28

<210> SEQ ID NO 1

<211> LENGTH: 8
<212> TYPE: PRT
<213> ORGANISM: Artificial sequence
<220> FEATURE:
<223> OTHER INFORMATION: heavy chain CDR1 of 12H5

<400> SEQUENCE: 1

Gly Tyr Thr Phe Thr Lys Asn Gly
1 5

<210> SEQ ID NO 2
<211> LENGTH: 8
<212> TYPE: PRT
<213> ORGANISM: Artificial sequence
<220> FEATURE:
<223> OTHER INFORMATION: heavy chain CDR2 of 12H5

<400> SEQUENCE: 2

Ile Asn Thr Tyr Thr Gly Glu Pro
1 5

<210> SEQ ID NO 3
<211> LENGTH: 10
<212> TYPE: PRT
<213> ORGANISM: Artificial sequence
<220> FEATURE:
<223> OTHER INFORMATION: heavy chain CDR3 of 12H5

<400> SEQUENCE: 3

Ala Arg Met Val Arg Asp Ala Met Asp Phe
1 5 10

<210> SEQ ID NO 4
<211> LENGTH: 10
<212> TYPE: PRT
<213> ORGANISM: Artificial sequence
<220> FEATURE:
<223> OTHER INFORMATION: light chain CDR1 of 12H5

<400> SEQUENCE: 4

Gln Ser Val Asp Phe Asp Gly Tyr Asn Tyr
1 5 10

<210> SEQ ID NO 5
<211> LENGTH: 3
<212> TYPE: PRT
<213> ORGANISM: Artificial sequence
<220> FEATURE:
<223> OTHER INFORMATION: light chain CDR2 of 12H5

<400> SEQUENCE: 5

Ala Ala Ser
1

<210> SEQ ID NO 6
<211> LENGTH: 9
<212> TYPE: PRT
<213> ORGANISM: Artificial sequence
<220> FEATURE:
<223> OTHER INFORMATION: light chain CDR3 of 12H5

<400> SEQUENCE: 6

Gln Gln Ser Asn Glu Asp Pro Tyr Thr
1 5

<210> SEQ ID NO 7
<211> LENGTH: 8

```
<212> TYPE: PRT
<213> ORGANISM: Artificial sequence
<220> FEATURE:
<223> OTHER INFORMATION: heavy chain CDR1 of G10D10

<400> SEQUENCE: 7

Gly Tyr Thr Phe Thr Lys Tyr Gly
1               5


<210> SEQ ID NO 8
<211> LENGTH: 8
<212> TYPE: PRT
<213> ORGANISM: Artificial sequence
<220> FEATURE:
<223> OTHER INFORMATION: heavy chain CDR2 of G10D10

<400> SEQUENCE: 8

Ile Asn Thr Tyr Thr Gly Glu Pro
1               5


<210> SEQ ID NO 9
<211> LENGTH: 10
<212> TYPE: PRT
<213> ORGANISM: Artificial sequence
<220> FEATURE:
<223> OTHER INFORMATION: heavy chain CDR3 of G10D10

<400> SEQUENCE: 9

Ala Arg Met Gly Arg Asp Ala Met Asp Tyr
1               5                   10


<210> SEQ ID NO 10
<211> LENGTH: 10
<212> TYPE: PRT
<213> ORGANISM: Artificial sequence
<220> FEATURE:
<223> OTHER INFORMATION: light chain CDR1 of G10D10

<400> SEQUENCE: 10

Gln Ser Val Asp Phe Asp Gly Tyr Ile Tyr
1               5                   10


<210> SEQ ID NO 11
<211> LENGTH: 3
<212> TYPE: PRT
<213> ORGANISM: Artificial sequence
<220> FEATURE:
<223> OTHER INFORMATION: light chain CDR2 of G10D10

<400> SEQUENCE: 11

Ala Ala Ser
1


<210> SEQ ID NO 12
<211> LENGTH: 9
<212> TYPE: PRT
<213> ORGANISM: Artificial sequence
<220> FEATURE:
<223> OTHER INFORMATION: light chain CDR3 of G10D10

<400> SEQUENCE: 12

Gln Gln Ser Arg Glu Asp Pro Trp Thr
1               5


<210> SEQ ID NO 13
<211> LENGTH: 8
<212> TYPE: PRT
```

```
<213> ORGANISM: Artificial sequence
<220> FEATURE:
<223> OTHER INFORMATION: heavy chain CDR1 of 8F11

<400> SEQUENCE: 13

Gly Tyr Thr Phe Thr Asn Tyr Gly
1               5


<210> SEQ ID NO 14
<211> LENGTH: 8
<212> TYPE: PRT
<213> ORGANISM: Artificial sequence
<220> FEATURE:
<223> OTHER INFORMATION: heavy chain CDR2 of 8F11

<400> SEQUENCE: 14

Ile Asn Thr Tyr Ser Gly Glu Pro
1               5


<210> SEQ ID NO 15
<211> LENGTH: 10
<212> TYPE: PRT
<213> ORGANISM: Artificial sequence
<220> FEATURE:
<223> OTHER INFORMATION: heavy chain CDR3 of 8F11

<400> SEQUENCE: 15

Ala Ser Leu Arg Arg Asp Ala Met Asp His
1               5                   10


<210> SEQ ID NO 16
<211> LENGTH: 10
<212> TYPE: PRT
<213> ORGANISM: Artificial sequence
<220> FEATURE:
<223> OTHER INFORMATION: light chain CDR1 of 8F11

<400> SEQUENCE: 16

His Ser Val Asp Phe Asp Gly Tyr Val Tyr
1               5                   10


<210> SEQ ID NO 17
<211> LENGTH: 3
<212> TYPE: PRT
<213> ORGANISM: Artificial sequence
<220> FEATURE:
<223> OTHER INFORMATION: light chain CDR2 of 8F11

<400> SEQUENCE: 17

Ala Ala Ser
1


<210> SEQ ID NO 18
<211> LENGTH: 9
<212> TYPE: PRT
<213> ORGANISM: Artificial sequence
<220> FEATURE:
<223> OTHER INFORMATION: light chain CDR3 of 8F11

<400> SEQUENCE: 18

Gln Gln Ser Arg Glu Asp Pro Trp Thr
1               5


<210> SEQ ID NO 19
<211> LENGTH: 25
<212> TYPE: DNA
<213> ORGANISM: Artificial sequence
```

<220> FEATURE:
<223> OTHER INFORMATION: primer

<400> SEQUENCE: 19
ccgtttgkat ytccagcttg gtscc 25

<210> SEQ ID NO 20
<211> LENGTH: 25
<212> TYPE: DNA
<213> ORGANISM: Artificial sequence
<220> FEATURE:
<223> OTHER INFORMATION: primer

<400> SEQUENCE: 20
cggtgaccgw ggtbccttgr cccca 25

<210> SEQ ID NO 21
<211> LENGTH: 26
<212> TYPE: DNA
<213> ORGANISM: Artificial sequence
<220> FEATURE:
<223> OTHER INFORMATION: primer

<400> SEQUENCE: 21
atggrcagrc ttacwtyytc attcct 26

<210> SEQ ID NO 22
<211> LENGTH: 31
<212> TYPE: DNA
<213> ORGANISM: Artificial sequence
<220> FEATURE:
<223> OTHER INFORMATION: primer

<400> SEQUENCE: 22
atgtggggay cgktttyamm cttttcaatt g 31

<210> SEQ ID NO 23
<211> LENGTH: 29
<212> TYPE: DNA
<213> ORGANISM: Artificial sequence
<220> FEATURE:
<223> OTHER INFORMATION: primer

<400> SEQUENCE: 23
atggvttggs tgtggamctt gcyattcct 29

<210> SEQ ID NO 24
<211> LENGTH: 25
<212> TYPE: DNA
<213> ORGANISM: Artificial sequence
<220> FEATURE:
<223> OTHER INFORMATION: primer

<400> SEQUENCE: 24
atggagacag acacactcct gctat 25

<210> SEQ ID NO 25
<211> LENGTH: 29
<212> TYPE: DNA
<213> ORGANISM: Artificial sequence
<220> FEATURE:
<223> OTHER INFORMATION: primer

<400> SEQUENCE: 25
atggvttggs tgtggamctt gcyattcct 29

-continued

```
<210> SEQ ID NO 26
<211> LENGTH: 27
<212> TYPE: DNA
<213> ORGANISM: Artificial sequence
<220> FEATURE:
<223> OTHER INFORMATION: primer

<400> SEQUENCE: 26

atggtyctya tvtccttgct gttctgg                                           27


<210> SEQ ID NO 27
<211> LENGTH: 20
<212> TYPE: DNA
<213> ORGANISM: Artificial sequence
<220> FEATURE:
<223> OTHER INFORMATION: primer

<400> SEQUENCE: 27

agttggaaca atggtgatgg                                                   20


<210> SEQ ID NO 28
<211> LENGTH: 23
<212> TYPE: DNA
<213> ORGANISM: Artificial sequence
<220> FEATURE:
<223> OTHER INFORMATION: primer

<400> SEQUENCE: 28

ttccggctct ctctcacttg atc                                               23
```